United States Patent [19]

Krause et al.

[11] Patent Number: 4,820,839

[45] Date of Patent: Apr. 11, 1989

[54] NITROGEN-CONTAINING HETEROCYCLIC ESTERS

[75] Inventors: Joachim Krause, Dieburg; Andreas Wächtler, Griesheim; Volker Reiffenrath, Darmstadt-Eberstadt, all of Fed. Rep. of Germany; Bernhard Scheuble, Yokohama, Japan; Reinhard Hittich, Modautal, Fed. Rep. of Germany

[73] Assignee: Merck Patent Gesellschaft Mit Beschrankter Haftung, Darmstadt, Fed. Rep. of Germany

[21] Appl. No.: 9,329

[22] PCT Filed: May 16, 1986

[86] PCT No.: PCT/EP86/00293

§ 371 Date: Jan. 23, 1987

§ 102(e) Date: Jan. 23, 1987

[87] PCT Pub. No.: WO86/07055

PCT Pub. Date: Dec. 4, 1986

[30] Foreign Application Priority Data

May 24, 1985 [DE] Fed. Rep. of Germany ....... 3518734

[51] Int. Cl.$^4$ ..................... C09K 19/34; C02F 1/13; C07D 239/02

[52] U.S. Cl. ................... 544/316; 252/299.5; 252/299.61; 252/299.01; 350/350 R; 350/350 S; 544/179; 544/180; 544/215; 544/219; 544/224; 544/238; 544/239; 544/241; 544/242; 544/295; 544/296; 544/298; 544/315; 544/318; 544/335; 546/275; 546/286; 546/288; 546/298; 546/300; 546/301; 546/302; 546/326; 546/328; 546/320; 546/240; 546/342; 546/339

[58] Field of Search ........... 252/299.5, 299.61, 299.01; 350/350 R, 350 S; 544/215, 219, 180, 179, 224, 239, 238, 241, 242, 295, 296, 298, 316, 315, 318, 335

[56] References Cited

U.S. PATENT DOCUMENTS

| 4,256,656 | 3/1981 | Beguin et al. | 252/299.61 |
|---|---|---|---|
| 4,311,610 | 1/1982 | Zaschke et al. | 252/299.61 |
| 4,358,393 | 11/1982 | Zaschke et al. | 252/299.61 |
| 4,460,770 | 7/1984 | Petrzilka et al. | 252/299.61 |
| 4,510,064 | 4/1985 | Eidenschink et al. | 252/299.61 |
| 4,512,636 | 4/1985 | Andrens et al. | 252/299.61 |
| 4,592,857 | 6/1986 | Sugimori et al. | 252/299.63 |
| 4,601,846 | 7/1986 | Demus et al. | 252/299.61 |
| 4,621,901 | 11/1986 | Petrzilka et al. | 252/299.61 |
| 4,623,477 | 11/1986 | Ogawa et al. | 252/299.61 |
| 4,640,795 | 2/1987 | Ogawa et al. | 252/299.61 |
| 4,642,199 | 2/1987 | Sugimori et al. | 252/299.61 |
| 4,659,500 | 4/1987 | Sugimori et al. | 252/299.61 |
| 4,659,502 | 4/1987 | Feardon et al. | 252/299.61 |
| 4,668,426 | 5/1987 | Demus et al. | 252/299.61 |
| 4,676,604 | 6/1987 | Petrazilra et al. | 252/299.61 |
| 4,683,078 | 7/1987 | Sugimori et al. | 252/299.61 |
| 4,684,220 | 8/1987 | Shionozaki et al. | 252/299.01 |
| 4,713,197 | 12/1987 | Eideyschink et al. | 252/299.61 |
| 4,721,367 | 1/1988 | Yoshimaga et al. | 252/299.61 |
| 4,723,005 | 2/1988 | Huymh-bh et al. | 252/299.61 |
| 4,752,414 | 6/1988 | Eidenschink et al. | 252/299.61 |
| 4,753,752 | 6/1988 | Raymes et al. | 252/299.61 |
| 4,756,847 | 7/1988 | Yoshida et al. | 252/299.61 |

FOREIGN PATENT DOCUMENTS

| 56501 | 7/1982 | European Pat. Off. | 252/299.61 |
|---|---|---|---|
| 84194 | 7/1983 | European Pat. Off. | 252/299.61 |
| 149238 | 7/1985 | European Pat. Off. | 252/299.61 |
| 225195 | 6/1987 | European Pat. Off. | 252/299.61 |
| 145912 | 1/1981 | Fed. Rep. of Germany | 252/299.61 |
| 3315295 | 10/1984 | Fed. Rep. of Germany | 252/299.61 |
| 3404116 | 8/1985 | Fed. Rep. of Germany | 252/299.61 |
| 3404117 | 8/1985 | Fed. Rep. of Germany | 252/299.61 |
| 3411571 | 10/1985 | Fed. Rep. of Germany | 252/299.61 |
| 3500897 | 7/1986 | Fed. Rep. of Germany | 252/299.61 |
| 3500909 | 8/1986 | Fed. Rep. of Germany | 252/299.61 |
| 3506446 | 8/1986 | Fed. Rep. of Germany | 252/299.61 |
| 3515373 | 11/1986 | Fed. Rep. of Germany | 252/299.61 |
| 3515633 | 11/1986 | Fed. Rep. of Germany | 252/299.61 |
| 3600052 | 7/1987 | Fed. Rep. of Germany | 252/299.61 |
| 56-164171 | 12/1981 | Japan | 252/299.61 |
| 56-164170 | 12/1981 | Japan | 252/299.61 |
| 60-78972 | 5/1985 | Japan | 252/299.61 |
| 61-17571 | 1/1986 | Japan | 252/299.61 |
| 61-167671 | 7/1986 | Japan | 252/299.61 |
| 61-260067 | 11/1986 | Japan | 252/299.61 |
| 61-281192 | 12/1986 | Japan | 252/299.61 |
| 62-22889 | 1/1987 | Japan | 252/299.61 |
| 62-00071 | 1/1987 | Japan | 252/299.61 |
| 8600087 | 1/1986 | PCT Int'l Appl. | 252/299.61 |
| 8600067 | 1/1986 | PCT Int'l Appl. | 252/299.61 |
| 8606401 | 11/1986 | PCT Int'l Appl. | 252/299.61 |

OTHER PUBLICATIONS

Green, D. C., et al., IBM Tech. Discl. Bull., vol. 15, No. 8, pp. 2467–2468 (Jan. 1973).

Pavlucheived, A. I., et al., J. De Physique, Coll. C3, Suppl. No. 4, vol. 40, pp. 63-1-4 (Apr. 1979).

Demus, D., et al., Flüssige Kristalle in Tabellen II, Veb Deutscher Verlag Für Grundstoff Industrie, Leipzig, pp. 344–400 (1984).

Gray, G. W., et al., Liquid Crystals & Plastic Crystals, vol. 1, John Wiley & Sons, N.Y., pp. 165, 166, 142, 143 (1974).

Primary Examiner—Teddy S. Gron
Attorney, Agent, or Firm—Millen & White

[57] ABSTRACT

Nitrogen-containing heterocyclic esters of the formula I,

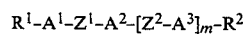

in which $R^1$, $R^2$, $A^1$, $A^2$, $A^3$, $Z^1$, $Z^2$ and m have the meaning specified in patent claim 1, are suitable as components of smectic liquid-crystalline phases.

16 Claims, No Drawings

NITROGEN-CONTAINING HETEROCYCLIC ESTERS

The invention relates to nitrogen-containing heterocyclic esters of the formula IV $$R^1-A^1-Z^1-A^2-[Z^2-A^3]_m-R^2 \qquad IV$$

in which
$R^1$ and $R^2$ are each an alkyl group, having 1 to 12 C atoms, in which one or more non-neighbouring $CH_2$ groups may also be replaced by —O—, —CO—, —O—CO—, —O—COO—, —CO—O— and/or —CH=CH—, or one of the radicals $R^1$ and $R^2$ is also H, F, Cl, Br or CN,
$A^1$ is 4,4'-biphenyl, in which one or more CH groups are replaced by N, which is unsubstituted or substituted by one or two F and/or Cl and/or Br atoms and/or $CH_3$ and/or CN groups,
$A^2$ and $A^3$ are each trans-1,4-cyclohexylene, or 1,4-phenylene, in which one or more CH groups may also be replaced by N, which is unsubstituted or substituted by one or two F and/or Cl atoms and/or Br atoms and/or $CH_3$ and/or CN groups,
$Z^1$ is —CO—O— or —O—CO—,
$Z^2$ is —CO—O—, —O—CO—, —CH$_2$CH$_2$—, —CH$_2$O—, —O—CH$_2$— or a single bond, and
m is 0 or 1,
with the provisos that
(1) the compounds contains (sic) at least one laterally substituted 1,4-phenylene group and
(2) in the case of m=0 and

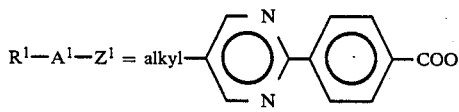

$A^2$ is 1,4-phenylene which is laterally substituted by fluorine or is 1,4-phenylene which is substituted, in the ortho position to $R^2$, by Cl, Br, $CH_3$ or CN, and also relates to the preparation of the compounds of the formula IV, liquid-crystalline phases containing compounds of the formula IV, the use thereof as components of liquid-crystalline phases, and also smectic liquid-crystalline phases, particularly chiral tilted smectic phases, containing compounds of the formula IV.

Chiral tilted smectic liquid-crystalline phases having ferroelectric properties can be prepared by adding one or more tilted smectic phases having a suitable chiral doping substance to the basic mixtures (L. A. Beresnev et al., Mol. Cryst. Liq. Cryst. 89, 327 (1982); H. R. Brand et al., J. Physique 44 (lett.), L-771 (1983). Such phases can be used as dielectrics for rapidly switching displays, which are based on the principle of SSFLC technology, described by Clark and Lagerwall (N. A. Clark and S. T. Lagerwall, Appl. Phys. Lett. 36, 899 (1980); U.S. Pat. No. 4,367,924) based on the ferroelectric properties of the chirally tilted phase. In this phase, the elongated molecules are arranged in layers, the molecules having a tilt angle to the layer perpendiculars. When proceeding from layer to layer, the tilt direction changes through a small angle relative to an axis which is perpendicular to the layers, so that a helical structure is formed. In displays which are based on the principle of SSFLC technology, the smectic layers are arranged perpendicular to the plates of the cell. The helical arrangement of the tilt directions of the molecules is suppressed by a very small spacing of the plates (about 1-2 μm). The longitudinal axes of the molecules are thereby forced to align themselves in a plane parallel to the plates of the cell, two distinct tilt or orientations being produced. Switching to and fro between these two states can be accomplished in the liquid-crystalline phase, which has a spontaneous polarization, by applying a suitable electrical alternating field. This switching process is significantly faster than the conventional twisted cells (TN-LCDs), which are based on nematic liquid crystals.

The low chemical, thermal and light stability of the currently available materials having chirally tilted smectic phases (such as, for example, Sc*) is a great disadvantage for many applications. A further disadvantageous property of displays based on the currently available chirally tilted smectic mixtures is that the spontaneous polarization has values which are too small, so that the switching time behaviour of the displays is unfavourably influenced and/or the pitch and the tilt of the phases do not correspond to the requirements of display technology. In addition, the temperature range of the ferroelectric phases is usually too small and is mainly at temperatures which are too high.

It has now been found that the use of the compounds of the formula IV as components of chirally tilted smectic mixtures can essentially reduce the disadvantages mentioned. The compounds of the formula IV are thus extremely suitable as components of chirally tilted smectic liquid-crystalline phases. In particular, especially chemically stable chirally tilted smectic liquid-crystalline phases having favourable ferroelectric phase regions, particularly having broad Sc* phase regions, excellent supercoolability to temperatures well below 0° C. without crystallization occurring (even phases according to the invention having a melting point above 0° C. can generally be supercooled to well below 0° C.), favourable degree of pitch, and values for the spontaneous polarization which are high for such phases can be prepared with their aid. P is the spontaneous polarization in $nC/cm^2$.

Similar compounds are known, for example, from German Offenlegungsschrift 3,506,446. However, the compounds specified therein are not ester compounds, in contrast to the present compounds.

The compounds of the formula IV can be used, as can similar compounds, as chiral doping substances for liquid-crystalline phases, but particularly as components of ferroelectric liquid-crystalline phases. These phases are suitable for displays which are based on the principle of the twisted cell (TN-displays), the guest-host effect, the effect of dynamic scattering, but particularly for ferroelectric displays, for example according to N. A. Clark and S. T. Lagerwall, Applied Phys. Lett. 36, 899 (1980).

The compounds of the formula IV have a broad field of application. Depending on the selection of substituents, these compounds can be used as base materials from which liquid-crystalline smectic materials are composed to a predominant extent; however, compounds of the formula I can also be added to liquid-crystalline base materials from other classes of compounds, for example in order to vary the dielectric and/or optical anisotropy and/or the viscosity and/or the spontaneous polarization and/or the phase regions and/or the tilt angle and/or the pitch of such a dielectric.

The compounds of the formula IV have high chemical stability. They are colourless and easily miscible with all conventional liquid crystals. Their use in liquid-crystalline phases leads to broader mesophase regions and improved values for the spontaneous polarization in chirally tilted smectic phases. The phases according to the invention are thus very well suited for liquid-crystalline phases for displays which are based on the principle of SSFLC technology. However, they are further suitable for other electro-optical display devices, such as, for example, TN cells or guest-host cells. In these, they serve to prevent reverse twist and to improve the elastic constants, besides extending the mesophase region.

The invention thus relates to compounds of the formula I and also to the use of the compounds of the formula I as components of liquid-crystalline phases. The invention furthermore relates to liquid-crystalline phases, particularly ferroelectric liquid-crystalline phases, containing at least one compound of the formula I, and also relates to liquid-crystalline display elements, particularly electro-optical display elements, which contain such phases.

For reasons of simplicity, Cy below is a 1,4-cyclohexylene group and Phe is a 1,4-phenylene group which may optionally also be substituted by one or two F and/or Cl atoms and/or $CH_3$ and/or CN groups (=Phe(F), Phe(Cl), Phe($CH_3$), Phe(CN)).

In the compounds of the formulae above and below, a substituted alkyl group or substituted ethylene are (sic) an alkyl group or $-CH_2CH_2-$ (ethylene) group which is mono- or polysubstituted on different C atoms by halogen, preferably fluorine or chlorine, or CN. The alkyl group is preferably only monosubstituted by halogen or CN. The C atom linked to halogen or CN is preferably an asymmetrical carbon atom.

One of the radicals $R^1$ and $R^2$ is preferably alkyl, —O—alkyl or oxaalkyl, —COO—alkyl, —OCO—alkyl, —CO—alkyl or alkenyl.

Alkenyl groups in the compounds of the formula I are preferably straight-chain trans-alkenyl groups of the formula

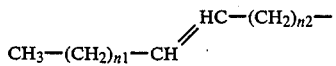

in which n2 is 0 to 10, preferably 2 to 10, and n1 is 0 to 5, preferably 0.

The alkyl radicals in the groups $R^1$ and/or $R^2$ may be straight-chain or branched. They are preferably straight-chain, have 5, 6, 7, 8, 9, 10, 11 or 12 C atoms and, accordingly, are preferably pentyl, hexyl, heptyl, octyl, nonyl, decyl, undecyl or dodecyl, furthermore methyl, ethyl, propyl or butyl.

If $R^1$ and/or $R^2$ are alkyl radicals in which one ("alkoxy" or "oxaalkyl") or two ("alkoxyalkoxy" or "dioxaalkyl") $CH_2$ groups are replaced by 0 atoms, then they may be straight-chain or branched. They are preferably straight-chain, have 5, 6, 7, 8, 9, 10, 11 or 12 C atoms and, accordingly, are preferably pentoxy, hexoxy, heptoxy, octoxy, nonoxy, decoxy, undecoxy, dodecoxy, 2-, 3- or 4-oxapentyl, 2-, 3-, 4- or 5-oxahexyl. 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl, 1,4-dioxaoctyl, 1,4,7-tri-oxaoctyl, 1,4-dioxanonyl or 1,4-dioxadecyl.

Compounds of the formula I and of the subformulae above and below having branched wing groups $R^1$ or $R^2$ may occasionally be important because of a higher solubility in the conventional liquid-crystalline base materials, but particularly as chiral doping substances for chirally tilted smectic phases, if they are optically active. However, such compounds are also suitable as components of nematic liquid-crystalline phases, particularly to prevent reverse twist. Branched groups of this type generally contain not more than one chain branch. Preferred branched radicals are isopropyl, 2-butyl (=1-methylpropyl), isobutyl (=2-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl and 2-octyloxy.

The asymmetrical carbon atom is preferably linked to two different substituted C atoms, one H atom and a substituent selected from the group comprising halogen (particularly F, Cl or Br), alkyl or alkoxy having 1 to 5 C atoms in each case, and CN. The optically active organic radical preferably has the formula

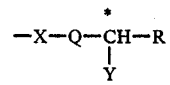

in which

X is —CO—O—, —O—CO—, —O—CO—O—, —CO—, —O—, —S—, —CH=CH—, —CH=CH—COO— or a single bond, Q is alkylene, having 1 to 5 C atoms, in which a $CH_2$ group, not linked to X, may also be replaced by —O—, —CO—, —O—CO—, —CO—O— or —CH=CH—, or a single bond, Y is CN, halogen, methyl or methoxy, and R is an alkyl group, having 1 to 18 C atoms, which is different to Y and in which one or two nonneighbouring $CH_2$ groups may also be replaced by —O—, —CO—, —O—CO—, —CO—O— and/or —CH=CH—.

X is preferably —CO—O—, —O—CO—, —O—, —CH=CH—COO— (trans) or a single bond. —O—, —CO—O— and —O—CO— are particularly preferred.

Q is preferably alkylene having 1 to 5 C atoms, or a single bond, particularly preferably —$CH_2$—, —$CH_2CH_2$— or a single bond.

Y is preferably $CH_3$, —CN or Cl, particularly preferably —CN or Cl.

R is preferably straight-chain alkyl, having 1 to 10, particularly having 1 to 7, C atoms, in which the $CH_2$ group which is linked to the asymmetrical C atom may optionally be replaced by —O—, —O—CO— Or —CO—O—.

$R^2$ in the formula I is preferably the optically active radical. Particularly preferred optically active radicals here correspond to the formula

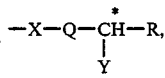

in which X is —O—, —CO—O— or —O—CO—, Q is —CH$_2$— or a single bond, Y is CH$_3$, and R is straight-chain alkyl, having 1 to 7 C atoms, in which the CH$_2$ group which is linked to the asymmetrical C atoms is replaced by —O—, —CO—O— or —O—CO—.

R$^1$ and R$^2$ are preferably alkyl or alkoxy groups having 3 to 10 C atoms in each case. They are preferably straight-chain. However, further preferred compounds of the formula III are those in which one of the groups R$^1$ and R$^2$ is a branched alkyl or alkoxy group.

Pyr is preferably linked to Phe in the 2-position.

Z$^1$ is preferably —O—CO—.

m is preferably 0.

The laterally substituted phenylene group is preferably a 1,4-phenylene group which is substituted by a F atom (=Phe(F)) or by a CN group (=Phe(CN)).

Further preferred compounds are those having a 2,3-dicyano-1,4-phenylene group (=Phe(CN)$_2$), particularly derivatives of 2,3-dicyanohydroquinone (=Phe(2-CN, 3-CN)).

—A$^1$— is preferably a structural element selected from the group comprising the formulae 1 to 4:

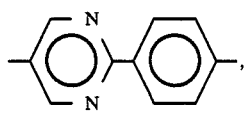 1

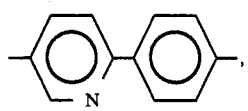 2

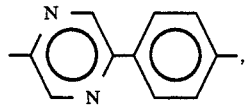 3

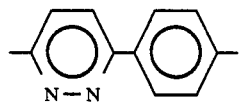 4

Groups of the formulae 1 and 2 are particularly preferred.

Amongst the compounds of the formula IV and the subformulae above and below, those are preferred in which at least one of the radicals contained therein has one of the preferred meanings specified. Particularly preferred smaller groups of compounds are those of the formulae IV1 to IV12:

| | |
|---|---|
| R$^1$—Pyr—Phe—OCO—Phe(F)—R$^2$ | IV1 |
| R$^1$—Pyr—Phe—COO—Phe(F)—R$^2$ | IV2 |
| R$^1$—Pyr—Phe—OCO—Phe(CN)—R$^2$ | IV3 |
| R$^1$—Pyr—Phe—COO—Phe(CN)—R$^2$ | IV4 |
| R$^1$—Phe—Pyr—OCO—Phe(F)—R$^2$ | IV5 |
| R$^1$—Phe—Pyr—COO—Phe(F)—R$^2$ | IV6 |
| R$^1$—Phe—Pyr—OCO—Phe(CN)—R$^2$ | IV7 |
| R$^1$—Phe—Pyr—COO—Phe(CN)—R$^2$ | IV8 |
| R$^1$—Pyr—Phe(F)—COO—A$^2$—R$^2$ | IV9 |
| R$^1$—Pyr—Phe(F)—OCO—A$^2$—R$^2$ | IV10 |
| R$^1$—Phe(F)—Pyr—OCO—A$^2$—R$^2$ | IV11 |
| R$^1$—Pyr—Phe—COO—Phe(Z—CN,3—CN)—R$^2$ | IV12 |

In the subformulae IV1, IV3, IV5 and IV12, R$^2$ is preferably alkoxy having 4 to 10 C atoms.

The compounds of the subformulae IV1, IV2, IV4, IV9, IV10 and IV12 are particularly preferred, and those of the subformulae IV1 and IV2, and furthermore IV13, are especially preferred.

Compounds of the formula IV which have no S$_c$ phases are likewise suitable as components of smectic phases according to the invention.

All compounds of the formula IV are prepared by methods which are known per se, as described in the literature (for example in the standard works such as Houben-Weyl, Methoden der Organischen Chemie [Methods of Organic Chemistry], Georg-Thieme-Verlag, Stuttgart), more precisely under reaction conditions which are known and suitable for the reactions mentioned. Use can also be made here of variants which are known per se, but which are not described in greater detail here.

The compounds of the formula IV can be prepared, for example, by esterification of an appropriate carboxylic acid, or one of the reactive derivatives thereof, using an appropriate alcohol, or one of the reactive derivatives thereof, by reaction of an appropriate amidine, or a derivative thereof, with a 2-acetyl-alkanal dialkylacetal, or with one of the reactive derivatives thereof, by replacement of the diazonium group in an appropriate diazonium salt by Cl, F or CN, or by reaction of an appropriate chlorine or bromine compound with a cyanide.

The ferroelectric liquid-crystalline phases according to the invention comprise 2 to 15, preferably 3 to 12, components, including at least one compound of the formula IV. The other components are preferably selected from the compounds of the formulae II to IV,

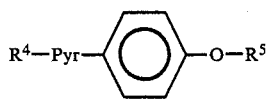 II

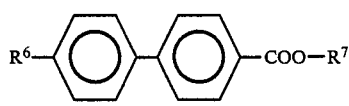 III

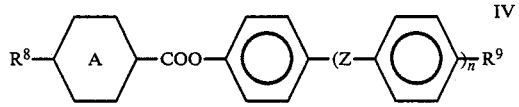 IV in which R$^4$ and R$^5$, in each case independently of one another, is (sic) n-alkyl having 5 to 12 C atoms, and R$^6$, R$^7$, R$^8$ and R$^9$, in each case independently of one another, is (sic) a straight-chain or branched, optionally chiral alkyl, alkoxy, alkoxycarbonyl or alkanoyloxy group having 5 to 12, particularly having 6 to 10, C atoms. Ring A is 1,4-phenylene or trans-1,4-cyclohexylene. n is 0 or 1.

All these substances can be prepared by methods which are known from the literature.

Furthermore preferred are ferroelectric phases, according to the invention, containing at least one compound of the formula V

     V in which

R¹ and R², in each case independently of one another, are a straight-chain alkyl group, having 1 to 15 C atoms, in which one or more nonneighbouring CH₂ groups may also be replaced by —O—, —S—, —CO—, CHCH₃—O—, —CHCH₃—, —CH—halogen—, CHCN—, —O—CO—, —O—COO—, —CO—O— and/or —CH=CH—,

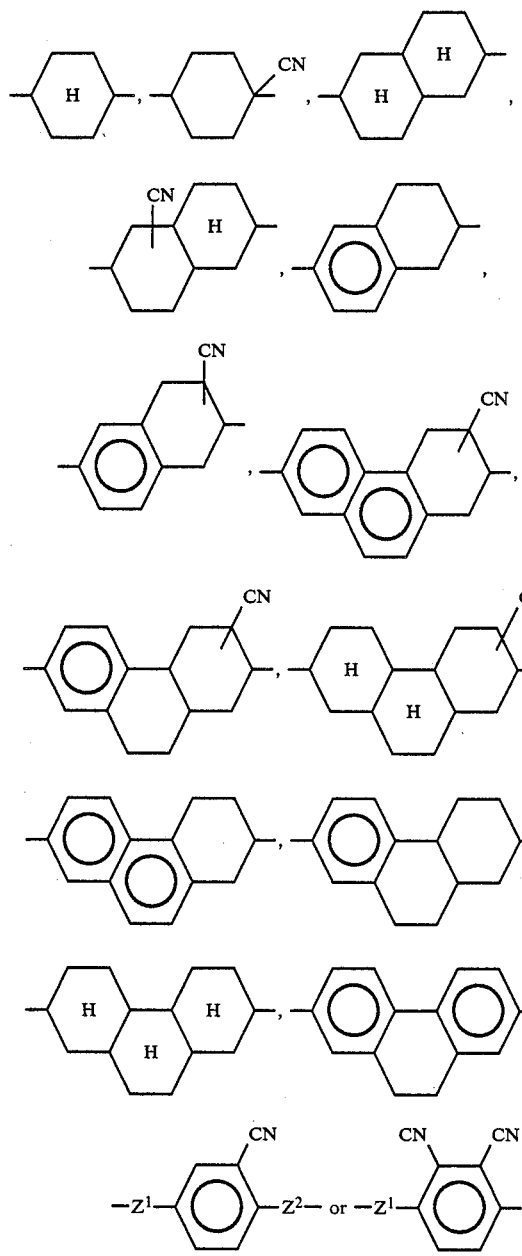

q is 0 or 1,

Q¹ and Q², in each case independently of one another, are —(A⁰—Z⁰)ₚ—, where

A⁰ is 1,4-cyclohexylene, which is unsubstituted or mono- or polysubstituted by halogen atoms, CH₃ and/or nitrile groups, in which one or two non-neighbouring CH₂ groups may also be replaced by —O— and/or —S— and/or a

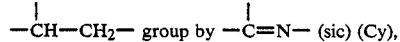

or 1,4-phenylene, which is unsubstituted or mono- or polysubstituted by halogen atoms, CH₃ and/or nitrile groups, in which one or more CH groups may also be replaced by N (Ph), one of the radicals A⁰ alternatively . . . (sic) 2,6-naphthylene (Na) or tetrahydro-2,6-naphthylene (4H-Na), optionally substituted by halogen or CN, Z⁰, Z¹ in each case independently of one another, and Z², are —CO—O—, —O—CO—, —CH₂O—, —OCH₂—, —CH₂CH₂—, —CHCNCH₂-, —CH₂—CHCN— or a single bond, and p is 1, 2 or 3, or, in the case of A=tetra- or octahydrophenanthrene, is alternatively 0, where, in the case of

A =

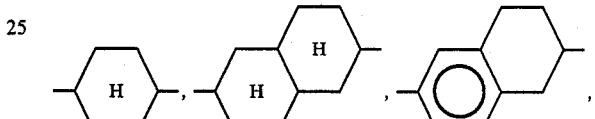

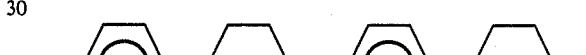

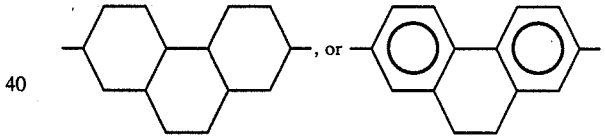

at least one group Z⁰ is —CHCNCH₂— or —CH₂CHCN—, and/or at least one CH₂ group in at least one of the groups R¹ and R² is replaced by —CHCN—.

The compounds of the formula V may have straight-chain or branched wing groups R¹ and/or R². Compounds having branched wing grouups may be used in the form of the racemate or as optically active compounds. Achiral basic mixtures of compounds of the formula V and, if appropriate, further achiral components may be doped with chiral compounds of the formula I or, additionally, with other chiral compounds in order to obtain chirally tilted smectic phases.

Particularly preferred smaller groups of compounds are those of the formulae V1 to V18:

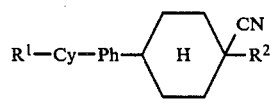    V1

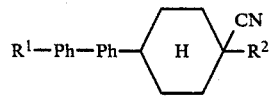    V2

-continued

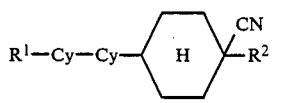 V3

 V4

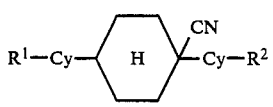 V5

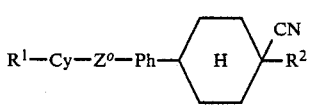 V6

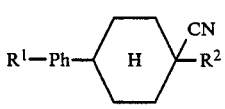 V7

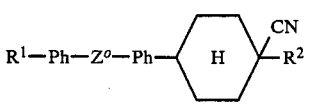 V8

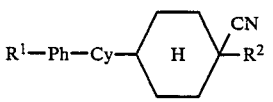 V9

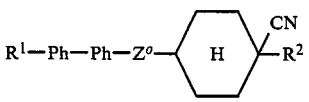 V10

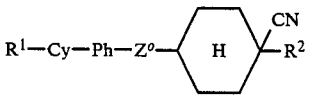 V11

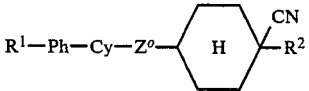 V12

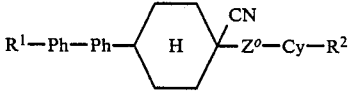 V13

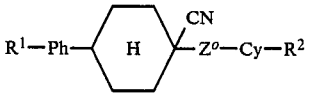 V14

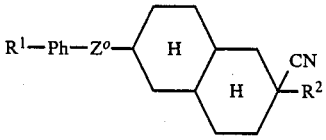 V15

-continued

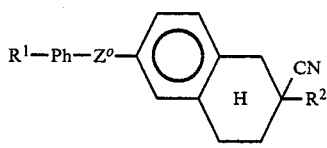 V16

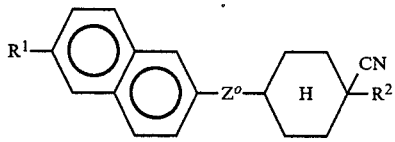 V17

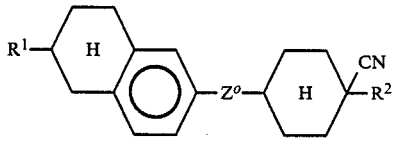 V18

A further particularly preferred smaller group of compounds are (sic) those of the formulae V19 to V22:

| | |
|---|---|
| $R^1-A^\circ-Cy-(CH_2)_r-CHCN-C_sH_{2s+1}$ | V19 |
| $R^1-A^\circ-A^\circ-Cy-(CH_2)_r-CHCN-C_sH_{2s+1}$ | V20 |
| $R^1-A^\circ-A^\circ-CHCN-CH_2-Cy-R^2$ | V21 |
| $R^1-A^\circ-A^\circ-CH_2-CHCN-Cy-R^2$ | V22 | in which r is 0, 1, 2 or 3 and (r+s) is 1 to 14.

Compounds of the formula V which have no $S_c$ phases are likewise suitable as components of smectic phases according to the invention.

All compounds of the formula V are prepared by methods which are known per se as described in the literature (for example in the standard works such as Houben-Weyl, Methoden der Organischen Chemie [Methods of Organic Chemistry], Georg-Thieme-Verlag, Stuttgart), more precisely under reaction conditions which are known and suitable for the reactions mentioned. Use may also be made here of variants which are known per se, but which are not described in greater detail here.

The formula V mainly covers known compounds, such as, for example, the preferred compounds described in German Offenlegungsschriften Nos. 3,231,707, 3,319,781, 3,320,024, 3,407,013, 3,443,029, 3,332,690, 3,332,691, 3,332,692, 2,933,563, 2,853,728, 2,613,293, 3,401,320, 3,136,624, 3,040,632, 3,205,766, 2,240,864, 2,937,700, 3,410,734, 3,324,686, European Offenlegungsschrift No. 0,085,995, European Offenlegungsschrift No. 0,084,194, DD No. 116,732, FR No. 2,425,469, FR No. 2,419,966, U.S. Pat. No. 4,237,026, U.S. Pat. No. 3,953,491, U.S. Pat. No. 4,225,454 or in H. J. Deutscher et al., J. prakt. Chemie, 321, 569 (1979) and J. C. Dubois et al., Mol. Cryst. Liq. Cryst. 47, 193 (1978).

Suitable components of the phases according to the invention are furthermore compounds of the formula

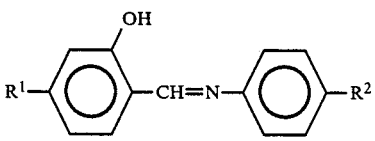

in which $R^1$ and $R^2$ have the meaning specified in the case of formula V.

Particularly preferred chirally tilted smectic liquid-crystalline phases according to the invention are those the achiral basic mixture of which contains, besides compounds of the formula IV, at least one other component having negative or small positive dielectric anisotropy. Compounds of the subformulae Va to Vp are suitable as further components having small positive or negative dielectric anisotropy:

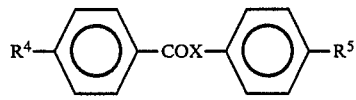
Va

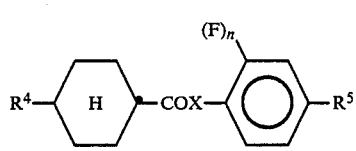
Vb

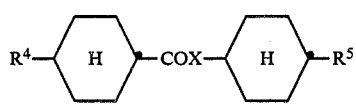
Vc

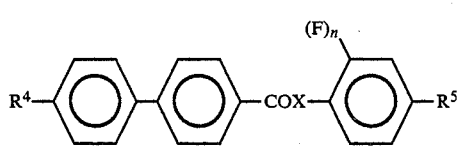
Vd

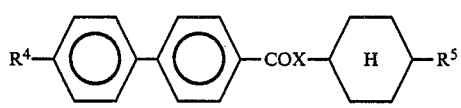
Ve

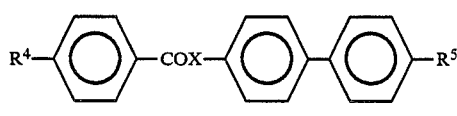
Vf

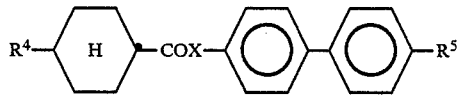
Vg

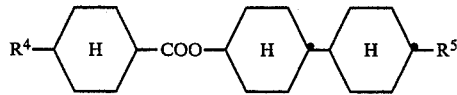
Vh

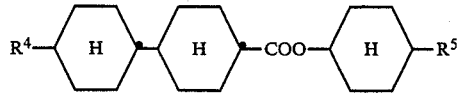
Vi

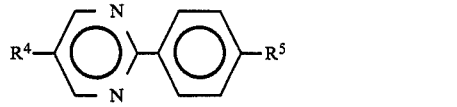
Vj

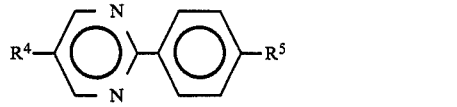
Vk

-continued

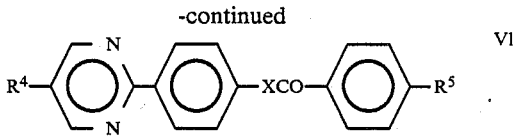
Vl

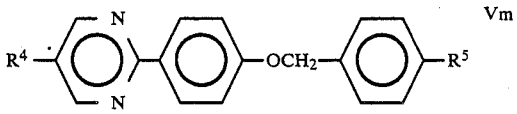
Vm

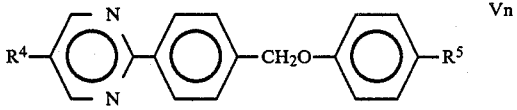
Vn

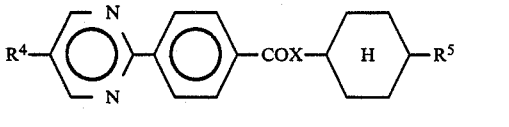
Vo

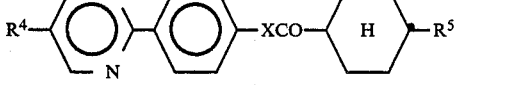
Vp $R^4$ and $R^5$ are in each case preferably straight-chain alkyl, alkoxy, alkanoyloxy or alkoxycarbonyl having 3 to 12 C atoms in each case. X is preferably 0. n is 0 or 1.

Particularly preferred compounds are those of the subformulae Va, Vb, Vd and Vf, in which $R^4$ and $R^5$ are in each case straight-chain alkyl or alkoxy having 5 to 10 C atoms in each case.

The compounds of the subformulae Vc, Vh and Vi are suitable as additives for lowering the melting point and are normally added to the basic mixtures in proportions of not more than 5%, preferably 1 to 3%. $R^4$ and $R^5$ in the compounds of the subformulae Vc, Vh and Vi are preferably straight-chain alkyl having 2 to 7, preferably 3 to 5, C atoms. A further suitable class of compounds for lowering the melting point in the phases according to the invention is that of the formula

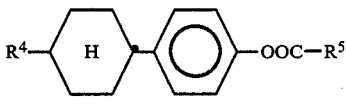

in which $R^4$ and $R^5$ have the preferred meaning specified for Vc, Vh and Vi.

Compounds containing the structural element B or C are furthermore suitable as further components having negative dielectric anisotropy.

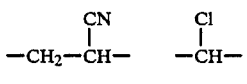

Preferred compounds of this type correspond to the formulae VIb and VIc:

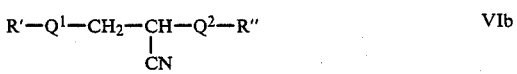
VIb

-continued $$R'-Q^3-Q^4-R''' \quad \text{VIc}$$

R' and R" are in each case preferably straight-chain alkyl or alkoxy groups having 2 to 10 C atoms in each case. $Q^1$ and $Q^2$ in each case denote 1,4-phenylene, trans-1,4-cyclohexylene, 4,4'-biphenylyl, 4-(trans-4-cyclohexyl)-phenyl, trans,trans-4,4'-bicyclohexyl, or one of the groups $Q^1$ and $Q^2$ is also a single bond.

$Q^3$ and $Q^4$ are in each case 1,4-phenylene, 4,4'-biphenylyl or trans-1,4-cyclohexylene. One of the groups $Q^3$ and $Q^4$ may also be 1,4-phenylene, in which at least one CH group is replaced by N. R'" is an optically active radical having an asymmetrical carbon atom of the structure

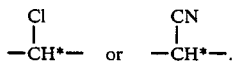

Particularly preferred compounds of the formula VIc are those of the formula VIc':

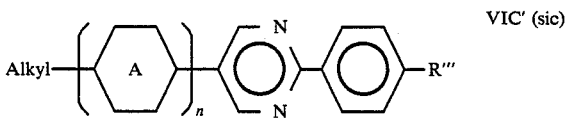

in which A is 1,4-phenylene or trans-1,4-cyclohexylene, and n is 0 or 1.

The phases according to the invention contain about 0.5–40%, preferably 5–10%, of one or more compounds of the formula I.

Furthermore preferred phases according to the invention are those containing 0.3–5%, preferably 1–4%, of one or more compounds of the formula I.

The dielectrics according to the invention are prepared in a fashion which is conventional per se. As a rule, the components are dissolved in one another, preferably at elevated temperature.

By means of suitable additives, the liquid-crystalline phases can be modified according to the invention in such a manner that they can be used in all types of liquid-crystal display elements which have hitherto become known.

The following examples are intended to describe the invention without limiting it. m.p.=melting point, c.p.=clear point. Above and below, percentage data are percent by weight; all temperature data are specified in degrees Celsius. The values for the spontaneous polarization are given for room temperature. Furthermore, C means solid crystalline condition, S means the smectic phase (the index characterizes the phase type), N means the nematic condition, Ch means the cholesteric phase, and I means the isotropic phase. The figure between the two symbols indicates the conversion temperatures in degrees Celsius. "Conventional work-up" means: water is added, the mixture is extracted with methylene chloride, the phases are separated, the organic phase is dried and evaporated, and the product is purified by crystallization and/or chromatography.

EXAMPLE 1

30 g of 2-fluoro-4-decyloxyl benzoic acid (prepared from 2-fluoro-4-hydroxybenzoic acid with decyl bromide in DMF/potassium carbonate) are refluxed with 15 g of thionyl chloride in 120 ml of toluene until the evolution of hydrogen chloride is complete, and then converted into the corresponding benzoyl chloride, and a mixture of 28.4 g of 4-(5-octylpyrimidin-2-yl)-phenyl and 10 ml of triethylamine is added. After stirring for 20 hours at 20°, the precipitated triethylammonium chloride is filtered off and the filtrate is concentrated. 4-(5-octylpyrimidin-2-yl)-phenyl 2-fluoro-4-decyloxybenzoate crystallizes.

The following are obtained analogously to this:

| | |
|---|---|
| 4-(5-propylpyrimidin-2-yl)-phenyl | 2-fluoro-4-butyloxybenzoate |
| 4-(5-pentylpyrimidin-2-yl)-phenyl | 2-fluoro-4-butyloxybenzoate |
| 4-(5-hexylpyrimidin-2-yl)-phenyl | 2-fluoro-4-butyloxybenzoate |
| 4-(5-heptylpyrimidin-2-yl)-phenyl | 2-fluoro-4-butyloxybenzoate |
| 4-(5-octylpyrimidin-2-yl)-phenyl | 2-fluoro-4-butyloxybenzoate |
| 4-(5-nonylpyrimidin-2-yl-phenyl | 2-fluoro-4-butyloxybenzoate |
| 4-(5-decylpyrimidin-2-yl)-phenyl | 2-fluoro-4-butyloxybenzoate |
| 4-(5-propylpyrimidin-2-yl)-phenyl | 2-fluoro-4-pentyloxybenzoate |
| 4-(5-pentylpyrimidin-2-yl)-phenyl | 2-fluoro-4-pentyloxybenzoate |
| 4-(5-hexylpyrimidin-2-yl)-phenyl | 2-fluoro-4-pentyloxybenzoate |
| 4-(5-heptylpyrimidin-2-yl)-phenyl | 2-fluoro-4-pentyloxybenzoate |
| 4-(5-octylpyrimidin-2-yl)-phenyl | 2-fluoro-4-pentyloxybenzoate |
| 4-(5-nonylpyrimidin-2-yl)-phenyl | 2-fluoro-4-pentyloxybenzoate |
| 4-(5-dicylpyrimidin-2-yl)-phenyl | 2-fluoro-4-pentyloxybenzoate |
| 4-(5-propylpyrimidin-2-yl)-phenyl | 2-fluoro-4-hexyloxybenzoate |
| 4-(5-pentylpyrimidin-2-yl)-phenyl | 2-fluoro-4-hexyloxybenzoate |
| 4-(5-hexylpyrimidin-2-yl)-phenyl | 2-fluoro-4-hexyloxybenzoate |
| 4-(5-heptylpyrimidin-2-yl)-phenyl | 2-fluoro-4-hexyloxybenzoate |
| 4-(5-octylpyrimidin-2-yl)-phenyl | 2-fluoro-4-hexyloxybenzoate |
| 4-(5-nonylpyrimidin-2-yl)-phenyl | 2-fluoro-4-hexyloxybenzoate |
| 4-(5-decylpyrimidin-2-yl)-phenyl | 2-fluoro-4-hexyloxybenzoate |
| 4-(5-propylpyrimidin-2-yl)-phenyl | 2-fluoro-4-heptyloxybenzoate |
| 4-(5-pentylpyrimidin-2-yl)-phenyl | 2-fluoro-4-heptyloxybenzoate |
| 4-(5-hexylpyrimidin-2-yl)-phenyl | 2-fluoro-4-heptyloxybenzoate |
| 4-(5-heptylpyrimidin-2-yl)-phenyl | 2-fluoro-4-heptyloxybenzoate |
| 4-(5-octylpyrimidin-2-yl)-phenyl | 2-fluoro-4-heptyloxybenzoate |
| 4-(5-nonylpyrimidin-2-yl)-phenyl | 2-fluoro-4-heptyloxybenzoate |

4-(5-decylpyrimidin-2-yl)-phenyl 2-fluoro-4-heptyloxybenzoate 4-(5-propylpyrimidin-2-yl)-phenyl 2-fluoro-4-oxtyloxybenzoate
4-(5-pentylpyrimidin-2-yl)-phenyl 2-fluoro-4-octyloxybenzoate
4-(5-hexylpyrimidin-2-yl)-phenyl 2-fluoro-4-octyloxybenzoate
4-(5-heptylpyrimidin-2-yl)-phenyl 2-fluoro-4-octyloxybenzoate
4-(5-octylpyrimidin-2-yl)-phenyl 2-fluoro-4-octyloxybenzoate
4-(5-nonylpyrimidin-2-yl)-phenyl 2-fluoro-4-octyloxybenzoate
4-(5-decylpyrimidin-2-yl)-phenyl 2-fluoro-4-octyloxybenzoate 4-(5-propylpyrimidin-2-yl)-phenyl 2-fluoro-4-nonyloxybenzoate
4-(5-pentylpyrimidin-2-yl)-phenyl 2-fluoro-4-nonyloxybenzoate
4-(5-hexylpyrimidin-2-yl)-phenyl 2-fluoro-4-nonyloxybenzoate
4-(5-heptylpyrimidin-2-yl)-phenyl 2-fluoro-4-nonyloxybenzoate
4-(5-octylpyrimidin-2-yl)-phenyl 2-fluoro-4-nonyloxybenzoate
4-(5-nonylpyrimidin-2-yl)-phenyl 2-fluoro-4-nonyloxybenzoate
4-(5-decylpyrimidin-2-yl)-phenyl 2-fluoro-4-nonyloxybenzoate 4-(5-propylpyrimidin-2-yl)-phenyl 2-fluoro-4-decyloxybenzoate
4-(5-pentylpyrimidin-2-yl)-phenyl 2-fluoro-4-decyloxybenzoate
4-(5-hexylpyrimidin-2-yl)-phenyl 2-fluoro-4-decyloxybenzoate
4-(5-heptylpyrimidin-2-yl)-phenyl 2-fluoro-4-decyloxybenzoate
4-(5-octylpyrimidin-2-yl)-phenyl 2-fluoro-4-decyloxybenzoate
4-(5-nonylpyrimidin-2-yl)-phenyl 2-fluoro-4-decyloxybenzoate
4-(5-decylpyrimidin-2-yl)-phenyl 2-fluoro-4-decyloxybenzoate 4-(5-propylpyrimidin-2-yl)-phenyl 3-fluoro-4-heptyloxybenzoate
4-(5-pentylpyrimidin-2-yl)-phenyl 3-fluoro-4-heptyloxybenzoate
4-(5-hexylpyrimidin-2-yl)-phenyl 3-fluoro-4-heptyloxybenzoate
4-(5-heptylpyrimidin-2-yl)-phenyl 3-fluoro-4-heptyloxybenzoate
4-(5-octylpyrimidin-2-yl)-phenyl 3-fluoro-4-heptyloxybenzoate
4-(5-nonylpyrimidin-2-yl)-phenyl 3-fluoro-4-heptyloxybenzoate, C 93° $S_c$ (88°) N 147° I
4-(5-decylpyrimidin-2-yl)-phenyl 3-fluoro-4-heptyloxybenzoate 4-(5-propylpyrimidin-2-yl)-phenyl 3-fluoro-4-octyloxybenzoate
4-(5-pentylpyrimidin-2-yl)-phenyl 3-fluoro-4-octyloxybenzoate
4-(5-hexylpyrimidin-2-yl)-phenyl 3-fluoro-4-octyloxybenzoate
4-(5-heptylpyrimidin-2-yl)-phenyl 3-fluoro-4-octyloxybenzoate
4-(5-octylpyrimidin-2-yl)-phenyl 3-fluoro-4-octyloxybenzoate
4-(5-nonylpyrimidin-2-yl)-phenyl 3-fluoro-4-octyloxybenzoate
4-(5-decylpyrimidin-2-yl)-phenyl 3-fluoro-4-octyloxybenzoate 4-(5-propylpyrimidin-2-yl)-phenyl 3-fluoro-4-nonyloxybenzoate
4-(5-pentylpyrimidin-2-yl)-phenyl 3-fluoro-4-nonyloxybenzoate
4-(5-hexylpyrimidin-2-yl)-phenyl 3-fluoro-4-nonyloxybenzoate
4-(5-heptylpyrimidin-2-yl)-phenyl 3-fluoro-4-nonyloxybenzoate
4-(5-octylpyrimidin-2-yl)-phenyl 3-fluoro-4-nonyloxybenzoate
4-(5-nonylpyrimidin-2-yl)-phenyl 3-fluoro-4-nonyloxybenzoate
4-(5-decylpyrimidin-2-yl)-phenyl 3-fluoro-4-nonyloxybenzoate 4-(5-propylprimidin-2-yl)-phenyl 3-chloro-4-hexyloxybenzoate
4-(5-pentylpyrimidin-2-yl)-phenyl 3-chloro-4-hexyloxybenzoate
4-(5-hexylpyrimidin-2-yl)-phenyl 3-chloro-4-hexyloxybenzoate
4-(5-heptylpyrimidin-2-yl)-phenyl 3-chloro-4-hexyloxybenzoate
4-(5-octylpyrimidin-2-yl)-phenyl 3-chloro-4-hexyloxybenzoate
4-(5-nonylpyrimidin-2-yl)-phenyl 3-chloro-4-hexyloxybenzoate
4-(5-decylpyrimidin-2-yl)-phenyl 3-chloro-4-hexyloxybenzoate 4-(5-propylpyrimidin-2-yl)-phenyl 3-chloro-4-heptyloxybenzoate
4-(5-pentylpyrimidin-2-yl)-phenyl 3-chloro-4-heptyloxybenzoate
4-(5-hexylpyrimidin-2-yl)-phenyl 3-chloro-4-heptyloxybenzoate
4-(5-heptylpyrimidin-2-yl)-phenyl 3-chloro-4-heptyloxybenzoate
4-(5-octylpyrimidin-2-yl)-phenyl 3-chloro-4-heptyloxybenzoate
4-(5-nonylpyrimidin-2-yl)-phenyl 3-chloro-4-heptyloxybenzoate
4-(5-decylpyrimidin-2-yl)-phenyl 3-chloro-4-heptyloxybenzoate 4-(5-propylpyrimidin-2-yl)-phenyl 3-chloro-4-octyloxybenzoate
4-(5-pentylpyrimidin-2-yl)-phenyl 3-chloro-4-octyloxybenzoate
4-(5-hexylpyrimidin-2-yl)-phenyl 3-chloro-4-octyloxybenzoate
4-(5-heptylpyrimidin-2-yl)-phenyl 3-chloro-4-octyloxybenzoate
4-(5-octylpyrimidin-2-yl)-phenyl 3-chloro-4-octyloxybenzoate
4-(5-nonylpyrimidin-2-yl)-phenyl 3-chloro-4-octyloxybenzoate 4-(5-decylpyrimidin-2-yl)-phenyl 3-chloro-4-octyloxybenzoate 4-(5-propylpyrimidin-2-yl)-phenyl 3-chloro-4-octyloxy)benzoate
4-(5-pentylpyrimidin-2-yl)-phenyl 3-chloro-4-(2-octyloxy)benzoate
4-(5-hexylpyrimidin-2-yl)-phenyl 3-chloro-4-(2-octyloxy)benzoate
4-(5-heptylpyrimidin-2-yl)-phenyl 3-chloro-4-(2-octyloxy)benzoate
4-(5-octylpyrimidin-2-yl)-phenyl 3-chloro-4-(2-octyloxy)benzoate
4-(5-nonylpyrimidin-2-yl)-phenyl 3-chloro-4-(2-octyloxy)benzoate, C 40° $S_c$ 42° Ch 56° I, $P_s=72$ nC/cm$^2$ at 25° in supercooled condition,
4-(5-decylpyrimidin-2-yl)-phenyl 3-chloro-4-(2-octyloxy)benzoate 4-(5-propylpyrimidin-2-yl)-phenyl 3-chloro-4-nonyloxybenzoate
4-(5-pentylpyrimidin-2-yl)-phenyl 3-chloro-4-nonyloxybenzoate
4-(5-hexylpyrimidin-2-yl)-phenyl 3-chloro-4-nonyloxybenzoate
4-(5-heptylpyrimidin-2-yl)-phenyl 3-chloro-4-nonyloxybenzoate
4-(5-octylpyrimidin-2-yl)-phenyl 3-chloro-4-nonyloxybenzoate
4-(5-nonylpyrimidin-2-yl)-phenyl 3-chloro-4-nonyloxybenzoate
4(5-decylpyrimidin-2-yl)-phenyl 3-chloro-4-nonyloxybenzoate 4-(5-propylpyrimidin-2-yl)-phenyl 3-bromo-4-hexyloxybenzoate
4-(5-pentylpyrimidin-2-yl)-phenyl 3-bromo-4-hexyloxybenzoate
4-(5-hexylpyrimidin-2-yl)-phenyl 3-bromo-4-hexyloxybenzoate
4-(5-heptylpyrimidin-2-yl)-phenyl 3-bromo-4-hexyloxybenzoate
4-(5-octylpyrimidin-2-yl)-phenyl 3-bromo-4-hexyloxybenzoate
4-(5-nonylpyrimidin-2-yl)-phenyl 3-bromo-4-hexyloxybenzoate
4-(5-decylpyrimidin-2-yl)-phenyl 3-bromo-4-hexyloxybenzoate 4-(5-propylpyrimidin-2-yl)-pheny 3-bromo-4-heptyloxybenzoate
4-(5-pentylpyrimidin-2-yl)-phenyl 3-bromo-4-heptyloxybenzoate
4-(5-hexylpyrimidin-2-yl)-phenyl 3-bromo-4-heptyloxybenzoate
4-(5-heptylpyrimidin-2-yl)-phenyl 3-bromo-4-heptyloxybenzoate
4-(5-octylpyrimidin-2-yl)-phenyl 3-bromo-4-heptyloxybenzoate
4-(5-nonylpyrimidin-2-yl)-phenyl 3-bromo-4-heptyloxybenzoate
4-(5-decylpyrimidin-2-yl)-phenyl 3-bromo-4-heptyloxybenzoate 4-(5-propylpyrimidin-2-yl)-phenyl 3-bromo-4-octyloxybenzoate
4-(5-pentylpyrimidin-2-yl)-phenyl 3-bromo-4-octyloxybenzoate
4-(5-hexylpyrimidin-2-yl)-phenyl 3-bromo-4-octyloxybenzoate
4-(5-heptylpyrimidin-2-yl)-phenyl 3-bromo-4-octyloxybenzoate, C 86° $S_c$ (79°) N 128° I
4-(5-octylpyrimidin-2-yl)-phenyl 3-bromo-4-octyloxybenzoate
4-(5-nonylpyrimidin-2-yl)-phenyl 3-bromo-4-octyloxybenzoate, C 80° $S_c$ 96° N 125° I
4-(5-decylpyrimidin-2-yl)-phenyl 3-bromo-4-octyloxybenzoate 4-(5-propylpyrimidin-2-yl)-phenyl 3-bromo-4-(2-octyloxy)benzoate
4-(5-pentylpyrimidin-2-yl)-phenyl 3-bromo-4-(2-octyloxy)benzoate
4-(5-hexylpyrimidin-2-yl)-phenyl 3-bromo-4-(2-octyloxy)benzoate
4-(5-heptylpyrimidin-2-yl)-phenyl 3-bromo-4-(2-octyloxy)benzoate
4(5-octylpyrimidin-2-yl)-phenyl 3-bromo-4-(2-octyloxy)benzoate
4-(5-nonylpyrimidin-2-yl)-phenyl 3-bromo-4-(2-octyloxy)benzoate
4-(5-decylpyrimidin-2-yl)-phenyl 3-bromo-4-(2-octyloxy)benzoate 4-(5-propylpyrimidin-2-yl)-phenyl 3-bromo-4-nonyloxybenzoate
4-(5-pentylpyrimidin-2-yl)-phenyl 3-bromo-4-nonyloxybenzoate
4-(5-hexylpyrimidin-2-yl)-phenyl 3-bromo-4-nonyloxybenzoate
4-(5-heptylpyrimidin-2-yl)-phenyl 3-bromo-4-nonyloxybenzoate
4-(5-octylpyrimidin-2-yl)-phenyl 3-bromo-4-nonyloxybenzoate
4-(5-nonylpyrimidin-2-yl)-phenyl 3-bromo-4-nonyloxybenzoate
4-(5-decylpyrimidin-2-yl)-phenyl 3-bromo-4-nonyloxybenzoate 4-(5-propylpyrimidin-2-yl)-phenyl 3-cyano-4-hexyloxybenzoate
4-(5-pentylpyrimidin-2-yl)-phenyl 3-cyano-4-hexyloxybenzoate
4-(5-hexylpyrimidin-2-yl)-phenyl 3-cyano-4-hexyloxybenzoate
4-(5-heptylpyrimidin-2-yl)-phenyl 3-cyano-4-hexyloxybenzoate
4-(5-octylpyrimidin-2-yl)-phenyl 3-cyano-4-hexyloxybenzoate
4-(5-nonylpyrimidin-2-yl)-phenyl 3-cyano-4-hexyloxybenzoate
4-(5-decylpyrimidin-2-yl)-phenyl 3-cyano-4-hexyloxybenzoate 4-(5-propylpyrimidin-2-yl)-phenyl 3-cyano-4-heptyloxybenzoate
4-(5-pentylpyrimidin-2-yl)-phenyl 3-cyano-4-heptyloxybenzoate
4-(5-hexylpyrimidin-2-yl)-phenyl 3-cyano-4-heptyloxybenzoate
4-(5-heptylpyrimidin-2-yl)-phenyl 3-cyano-4-heptyloxybenzoate
4-(5-octylpyrimidin-2-yl)-phenyl 3-cyano-4-heptyloxybenzoate
4-(5-nonylpyrimidin-2-yl)-phenyl 3-cyano-4-heptyloxybenzoate 4-(5-decylpyrimidin-2-yl)-phenyl 3-cyano-4-heptyloxybenzoate 4-(5-propylpyrimidin-2-yl)-phenyl 3-cyano-4-octyloxybenzoate 4-(5-pentylpyrimidin-2-yl)-phenyl 3-cyano-4-octyloxybenzoate 4-(5-hexylpyrimidin-2-yl)-phenyl 3-cyano-4-octyloxybenzoate 4-(5-heptylpyrimidin-2-yl)-phenyl 3-cyano-4-octyloxybenzoate 4-(5-octylpyrimidin-2-yl)-phenyl 3-cyano-4-octyloxybenzoate 4-(5-nonylpyrimidin-2-yl)-phenyl 3-cyano-4-octyloxybenzoate, C 66° $S_c$ 120° N 123° I 4-(5-decylpyrimidin-2-yl)-phenyl 3-cyano-4-octyloxybenzoate 4-(5-propylpyrimidin-2-yl)-phenyl 3-cyano-4-(2-octyloxy)benzoate 4-(5-pentylpyrimidin-2-yl)-phenyl 3-cyano-4-(2-octyloxy)benzoate 4-(5-hexylpyrimidin-2-yl)-phenyl 3-cyano-4-(2-octyloxy)benzoate 4-(5-heptylpyrimidin-2-yl)-phenyl 3-cyano-4-(2-octyloxy)benzoate 4-(5-octylpyrimidin-2-yl)-phenyl 3-cyano-4-(2-octyloxy)benzoate 4-(5-nonylpyrimidin-2-yl)-phenyl 3-cyano-4-(2-octyloxy)benzoate 4-(5-decylpyrimidin-2-yl)-phenyl 3-cyano-4-(2-octyloxy)benzoate 4-(5-propylpyrimidin-2-yl)-phenyl 3-cyano-4-nonyloxybenzoate 4-(5-pentylpyrimidin-2-yl)-phenyl 3-cyano-4-nonyloxybenzoate 4-(5-hexylpyrimidin-2-yl)-phenyl 3cyano-4-nonyloxybenzoate 4-(5-heptylpyrimidin-2-yl)-phenyl 3-cyano-4-nonyloxybenzoate 4-(5-octylpyrimidin-2-yl)-phenyl 3-cyano-4-nonyloxybenzoate 4-(5-nonylpyrimidin-2-yl)-phenyl 3-cyano-4-nonyloxybenzoate 4-(5-decylpyrimidin-2-yl)-phenyl 3-cyano-4-nonyloxybenzoate 4-(5-propylpyrimidin-2-yl)-phenyl 3-fluoro-4-heptylbenzoate 4-(5-pentylpyrimidin-2-yl)-phenyl 3-fluoro-4-heptylbenzoate 4-(5-hexylpyrimidin-2-yl)-phenyl 3-fluoro-4-heptylbenzoate 4-(5-heptylpyrimidin-2-yl)-phenyl 3-fluoro-4-heptylbenzoate 4-(5-octylpyrimidin-2-yl)-phenyl 3-fluoro-4-heptylbenzoate 4-(5-nonylpyrimidin-2-yl)-phenyl 3-fluoro-4-heptylbenzoate 4-(5-decylpyrimidin-2-yl)-phenyl 3-fluoro-4-heptylbenzoate 4-(5-propylpyrimidin-2-yl)-phenyl 3-fluoro-4-octylbenzoate 4-(5-pentylpyrimidin-2-yl)-phenyl 3-fluoro-4-octylbenzoate 4-(5-hexylpyrimidin-2-yl)-phenyl 3-fluoro-4-octylbenzoate 4-(5-heptylprimidin-2-yl)-phenyl 3-fluoro-4-octylbenzoate 4-(5-octylpyrimidin-2-yl)-phenyl 3-fluoro-4-octylbenzoate 4-(5-nonylpyrimidin-2-yl)-phenyl 3-fluoro-4-octylbenzoate 4-(5-decylpyrimidin-2-yl)-phenyl 3-fluoro-4-octybenzoate 4-(5-propylpyrimidin-2-yl)-phenyl 3-fluoro-4-nonylbenzoate 4-(5-pentylpyrimidin-2-yl)-phenyl 3-fluoro-4-nonylbenzoate 4-(5-hexylpyrimidin-2-yl)-phenyl 3-fluoro-4-nonylbenzoate 4-(5-heptylpyrimidin-2-yl)-phenyl 3-fluoro-4-nonylbenzoate 4-(5-octylpyrimidin-2-yl)-phenyl 3-fluoro-4-nonylbenzoate 4-(5-nonylpyrimidin-2-yl)-phenyl 3-fluoro-4-nonylbenzoate 4-(5-decylpyrimidin-2-yl)-phenyl 3-fluoro-4-nonylbenzoate 4-(5-propylpyrimidin-2-yl)-phenyl 3-chloro-4-hexylbenzoate 4-(5-pentylpyrimidin-2-yl)-phenyl 3-chloro-4-hexylbenzoate 4-(5-hexylpyrimidin-2-yl)-phenyl 3-chloro-4-hexylbenzoate 4-(5-heptylpyrimidin-2-yl)-phenyl 3-chloro-4-hexylbenzoate 4-(5-octylpyrimidin-2-yl)-phenyl 3-chloro-4-hexylbenzoate 4-(5-nonylpyrimidin-2-yl)-phenyl 3-chloro-4-hexylbenzoate 4-(5-decylpyrimidin-2-yl)-phenyl 3-chloro-4-hexylbenzoate 4-(5-propylpyrimidin-2-yl)-phenyl 3-chloro-4-heptylbenzoate 4-(5-pentylpyrimidin-2-yl)-phenyl 3-chloro-4-heptylbenzoate 4-(5-hexylpyrimidin-2-yl)-phenyl 3-chloro-4-heptylbenzoate 4-(5-hepthylpyrimidin-2-yl)-phenyl 3-chloro-4-heptylbenzoate 4-(5-octylpyrimidin-2-yl)-phenyl 3-chloro-4-heptylbenzoate 4-(5-nonylprimidin-2-yl)-phenyl 3-chloro-4-heptylbenzoate 4-(5-decylpyrimidin-2-yl)-phenyl 3-chloro-4-heptylbenzoate 4-(5-propylpyrimidin-2-yl)-phenyl 3-chloro-4-octylbenzoate 4(5-pentylpyrimidin-2-yl)-phenyl 3-chloro-4-octylbenzoate 4-(5-hexylpyrimidin-2-yl)-phenyl 3-chloro-4-octylbenzoate 4-(5-heptylpyrimidin-2-yl)-phenyl 3-chloro-4-octylbenzoate 4-(5-octylpyrimidin-2-yl)-phenyl 3-chloro-4-octylbenzoate 4-(5-nonylpyrimidin-2-yl)-phenyl 3-chloro-4-octylbenzoate 4-(5-decylpyrimidin-2-yl)-phenyl 3-chloro-4-octylbenzoate 4-(5-propylpyrimidin-2-yl)-phenyl 3-chloro-4-nonylbenzoate
4-(5-pentylpyrimidin-2-yl)-phenyl 3-chloro-4-nonylbenzoate
4-(5-hexylpyrimidin-2-yl)-phenyl 3-chloro-4-nonylbenzoate
4-(5-heptylpyrimidin-2-yl)-phenyl 3-chloro-4-nonylbenzoate
4-(5-octylpyrimidin-2-yl)-phenyl 3-chloro-4-nonylbenzoate
4-(5-nonylpyrimidin-2-yl)-phenyl 3-chloro-4-nonylbenzoate
4-(5-decylpyrimidin-2-yl)-phenyl 3-chloro-4-nonylbenzoate 4r(5-propylpyrimidin-2-yl)-phenyl 3-bromo-4-hexylbenzoate
4-(5-pentylpyrimidin-2-yl)-phenyl 3-bromo-4-hexylbenzoate
4-(5-hexylpyrimidin-2-yl)-phenyl 3-bromo-4-hexylbenzoate
4-(5-heptylpyrimidin-2-yl)-phenyl 3-bromo-4-hexylbenzoate
4-(5-octylpyrimidin-2-yl)-phenyl 3-bromo-4-hexylbenzoate
4-(5-nonylpyrimidin-2-yl)-phenyl 3-bromo-4-hexylbenzoate
4-(5-decylpyrimidin-2-yl)-phenyl 3-bromo-4-hexylbenzoate 4-(5-propylpyrimidin-2-yl)-phenyl 3-bromo-4-heptylbenzoate
4-(5-pentylpyrimidin-2-yl)-phenyl 3-bromo-4-heptylbenzoate
4-(5-hexylpyrimidin-2-yl)-phenyl 3-bromo-4-heptylbenzoate
4-(5-heptylpyrimidin-2-yl)-phenyl 3-bromo-4-heptylbenzoate
4-(5-octylpyrimidin-2-yl)-phenyl 3-bromo-4-heptylbenzoate
4-(5-nonylpyrimidin-2-yl)-phenyl 3-bromo-4-heptylbenzoate
4-(5-decylpyrimidin-2-yl)-phenyl 3-bromo-4-heptylbenzoate 4-(5-propylpyrimidin-2-yl)-phenyl 3-bromo-4-octylbenzoate
4-(5-pentylpyrimidin-2-yl)-phenyl 3-bromo-4-octylbenzoate
4-(5-hexylpyrimidin-2-yl)-phenyl 3-bromo-4-octylbenzoate, C 80° N 86° I
4-(5-heptylpyrimidin-2-yl)-phenyl 3-bromo-4-octylbenzoate, C 62° N 94° I
4-(5-octylpyrimidin-2-yl)-phenyl 3-bromo-4-octylbenzoate
4-(5-nonylpyrimidin-2-yl)-phenyl 3-bromo-4-octylbenzoate, C 51° $S_c$ 64° N 93° I
4-(5-decylpyrimidin-2-yl)-phenyl 3-bromo-4-octylbenzoate 4-(5-propylpyrimidin-2-yl)-phenyl 3-bromo-4-nonylbenzoate
4-(5-pentylpyrimidin-2-yl)-phenyl 3-bromo-4-nonylbenzoate
4-(5-hexylpyrimidin-2-yl)-phenyl 3-bromo-4-nonylbenzoate
4-(5-heptylpyrimidin-2-yl)-phenyl 3-bromo-4-nonylbenzoate
4-(5-octylpyrimidin-2-yl)-phenyl 3-bromo-4-nonylbenzoate
4-(5-nonylpyrimidin-2-yl)-phenyl 3-bromo-4-nonylbenzoate
4-(5-decylpyrimidin-2-yl)-phenyl 3-bromo-4-nonylbenzoate 4-(5-propylpyrimidin-2-yl)-phenyl 3-cyano-4-hexylbenzoate
4-(5-pentylpyrimidin-2-yl)-phenyl 3-cyano-4-hexylbenzoate
4-(5-hexylpyrimidin-2-yl)-phenyl 3-cyano-4-hexylbenzoate
4-(5-heptylpyrimidin-2-yl)-phenyl 3-cyano-4-hexylbenzoate
4-(5-octylpyrimidin-2-yl)-phenyl 3-cyano-4-hexylbenzoate
4-(5-nonylpyrimidin-2-yl)-phenyl 3-cyano-4-hexylbenzoate
4-(5-decylpyrimidin-2-yl)-phenyl 3-cyano-4-hexylbenzoate 4-(5-propylpyrimidin-2-yl)-phenyl 3-cyano-4-heptylbenzoate
4-(5-pentylpyrimidin-2-yl)-phenyl 3-cyano-4-heptylbenzoate
4-(5-hexylpyrimidin-2-yl)-phenyl 3-cyano-4-heptylbenzoate
4-(5-heptylpyrimidin-2-yl)-phenyl 3-cyano-4-heptylbenzoate
4-(5-octylpyrimidin-2-yl)-phenyl 3-cyano-4-heptylbenzoate
4-(5-nonylpyrimidin-2-yl)-phenyl 3-cyano-4-heptylbenzoate
4-(5-decylpyrimidin-2-yl)-phenyl 3-cyano-4-heptylbenzoate 4-(5-propylpyrimidin-2-yl)-phenyl 3-cyano-4-octylbenzoate
4-(5-pentylpyrimidin-2-yl)-phenyl 3-cyano-4-octylbenzoate
4-(5-hexylpyrimidin-2-yl)-phenyl 3-cyano-4-octylbenzoate
4-(5-heptylpyrimidin-2-yl)-phenyl 3-cyano-4-octylbenzoate
4-(5-octylpyrimidin-2-yl)-phenyl 3-cyano-4-octylbenzoate
4-(5-nonylpyrimidin-2-yl)-phenyl 3-cyano-4-octylbenzoate, C 88° $S_A$ (86°) N (87°) I
4-(5-decylpyrimidin-2-yl)-phenyl 3-cyano-4-octylbenzoate 4-(5-propylpyrimidin-2-yl)-phenyl 3-cyano-4-nonylbenzoate
4-(5-pentylpyrimidin-2-yl)-phenyl 3-cyano-4-nonylbenzoate
4-(5-hexylpyrimidin-2-yl)-phenyl 3-cyano-4-nonylbenzoate
4-(5-heptylpyrimidin-2-yl)-phenyl 3-cyano-4-nonylbenzoate
4-(5-octylpyrimidin-2-yl)-phenyl 3-cyano-4-nonylbenzoate
4-(5-nonylpyrimidin-2-yl)-phenyl 3-cyano-4-nonylbenzoate 4-(5-decylpyrimidin-2-yl)-phenyl 3-cyano-4-nonylbenzoate

EXAMPLE 2

17.0 g of 4-(5-decylpyrimidin-2-yl)-benzoic acid (prepared from 4-(5-decylpyrimidin-2-yl)-benzonitrile by saponification) and 11.1 g of 2-fluoro-4-nonylphenol are introduced into 200 ml of dichloromethane and 11.0 g of dicyclohexylcarbodiimide are added. The mixture is stirred for 4 hours at 20°, the precipitated urea is filtered off under suction, and the filtrate is concentrated to a small volume. After adsorptive filtration of the residue over silica gel using ethyl acetate as eluant, 2-fluoro-4-nonylphenyl 4-(5-decylpyrimidin-2-yl)-benzoate is obtained.

The following are obtained analogously:

2-fluoro-4-propylphenyl 4-(5-butylpyrimidin-2-yl)-benzoate
2-fluoro-4-pentylphenyl 4-(5-butylpyrimidin-2-yl)-benzoate
2-fluoro-4-hexylphenyl 4-(5-butylpyrimidin-2-yl)-benzoate
2-fluoro-4-heptylphenyl 4-(5-butylpyrimidin-2-yl)-benzoate
2-fluoro-4-octylphenyl 4-(5-butylpyrimidin-2-yl)-benzoate
2-fluoro-4-nonylphenyl 4-(5-butylpyrimidin-2-yl)-benzoate
2-fluoro-4-decylphenyl 4-(5-butylpyrimidin-2-yl)-benzoate 2-fluoro-4-propylphenyl 4-(5-pentylpyrimidin-2-yl)-benzoate
2-fluoro-4-pentylphenyl 4-(5-pentylpyrimidin-2-yl)-benzoate
2-fluoro-4-hexylphenyl 4-(5-pentylpyrimidin-2-yl)-benzoate
2-fluoro-4-heptylphenyl 4-(5-pentylpyrimidin-2-yl)-benzoate
2-fluoro-4-octylphenyl 4-(5-pentylpyrimidin-2-yl)-benzoate
2-fluoro-4-nonylphenyl 4-(5-pentylpyrimidin-2-yl)-benzoate
2-fluoro-4-decylphenyl 4-(5-pentylpyrimidin-2-yl)-benzoate 2-fluoro-4-propylphenyl 4-(5-hexylpyrimidin-2-yl)-benzoate
2-fluoro-4-pentylphenyl 4-(5-hexylpyrimidin-2-yl)-benzoate
2-fluoro-4-hexylphenyl 4-(5-hexylpyrimidin-2-yl)-benzoate
2-fluoro-4-heptylphenyl 4-(5-hexylpyrimidin-2-yl)-benzoate
2-fluoro-4-octylphenyl 4-(5-hexylpyrimidin-2-yl)-benzoate
2-fluoro-4-nonylphenyl 4-(5-hexylpyrimidin-2-yl)-benzoate
2-fluoro-4-decypheny 4-(5-hexylpyrimidin-2-yl)-benzoate 2-fluoro-4-propylpheny 4-(5-heptylpyrimidin-2-yl)-benzoate
2-fluoro-4-pentylphenyl 4-(5-heptylpyrimidin-2-yl)-benzoate
2-fluoro-4-hexylphenyl 4-(5-heptylpyrimidin-2-yl)-benzoate
2-fluoro-4-heptylphenyl 4-(5-heptylpyrimidin-2-yl)-benzoate
2-fluoro-4-octylphenyl 4-(5-heptylpyrimidin-2-yl)-benzoate
2-fluoro-4-nonylphenyl 4-(5-heptylpyrimidin-2-yl)-benzoate
2-fluoro-4-decylphenyl 4-(5-heptylpyrimidin-2-yl)-benzoate 2-fluoro-4-propylphenyl 4-(5-octylpyrimidin-2-yl)-benzoate
2-fluoro-4-pentylphenyl 4-(5-octylpyrimidin-2-yl)-benzoate
2-fluoro-4-hexylphenyl 4-(5-octylpyrimidin-2-yl)-benzoate
2-fluoro-4-heptylphenyl 4-(5-octylpyrimidin-2-yl)-benzoate
2-fluoro-4-octylphenyl 4-(5-octylpyrimidin-2-yl)-benzoate
2-fluoro-4-nonylphenyl 4-(5-octylpyrimidin-2-yl)-benzoate
2-fluoro-4-decylphenyl 4-(5-octylpyrimidin-2-yl)-benzoate 2-fluoro-4-propylphenyl 4-(5-nonylpyrimidin-2-yl)-benzoate
2-fluoro-4-pentylphenyl 4-(5-nonylpyrimidin-2-yl)-benzoate
2-fluoro-4-hexylphenyl 4-(5-nonylpyrimidin-2-yl)-benzoate
2-fluoro-4-heptylphenyl 4-(5-nonylpyrimidin-2-yl)-benzoate
2-fluoro-4-octylphenyl 4-(5-nonylpyrimidin-2-yl)-benzoate
2-fluoro-4-nonylphenyl 4-(5-nonylpyrimidin-2-yl)-benzoate
2-fluoro-4-decylphenyl 4-(5-nonylpyrimidin-2-yl)-benzoate 2-fluoro-4-propylphenyl 4-(5-decylpyrimidin-2-yl)-benzoate
2-fluoro-4-pentylphenyl 4-(5-decylpyrimidin-2-yl)-benzoate
2-fluoro-4-hexylphenyl 4-(5-decylpyrimidin-2-yl)-benzoate
2-fluoro-4-heptylphenyl 4-(5-decylpyrimidin-2-yl)-benzoate
2-fluoro-4-octylphenyl 4-(5-decylpyrimidin-2-yl)-benzoate
2-fluoro-4-nonylphenyl 4-(5-decylpyrimidin-2-yl)-benzoate
2-fluoro-4-decylphenyl 4-(5-decylpyrimidin-2-yl)-benzoate

EXAMPLE 3

29.8 g of 4-(5-heptylpyrimidin-2-yl)-benzoic acid (obtained from 4-(5-heptylpyrimidin-2-yl)-benzonitrile by saponification) and 25.9 g of 2-cyano-4-decylphenol are esterified with one another as described in Example 22 with addition of 21.0 g of dicyclohexylcarbodiimide. 2-Cyano-4-decylphenyl 4-(5-heptylpyrimidin-2-yl)-benzoate is obtained.

The following are obtained analogously:

2-cyano-4-propylpheny 4-(5-propylpyrimidin-2-yl)-benzoate
2-cyano-4-pentylphenyl 4-(5-propylpyrimidin-2-yl)-benzoate 2-cyano-4-hexylphenyl 4-(5-propylpyrimidin-2-yl)-benzoate
2-cyano-4-heptylphenyl 4-(5-propylpyrimidin-2-yl)-benzoate
2-cyano-4-octylphenyl 4-(5-propylpyrimidin-2-yl)-benzoate
2-cyano-4-nonylphenyl 4-(5-propylpyrimidin-2-yl)-benzoate
2-cyano-4-decylphenyl 4-(5-propylpyrimidin-2-yl)-benzoate 2-cyano-4-propylphenyl 4-(5-pentylpyrimidin-2-yl)-benzoate
2-cyano-4-pentylphenyl 4-(5-pentylpyrimidin-2-yl)-benzoate
2-cyano-4-hexylphenyl 4-(5-pentylpyrimidin-2-yl)-benzoate
2-cyano-4-heptylphenyl 4-(5-pentylpyrimidin-2-yl)-benzoate
2-cyano-4-octylphenyl 4-(5-pentylpyrimidin-2-yl)-benzoate
2-cyano-4-nonylphenyl 4-(5-pentylpyrimidin-2-yl)-benzoate
2-cyano-4-decylphenyl 4-(5-pentylpyrimidin-2-yl)-benzoate 2-cyano-4-propylphenyl 4-(5-hexylpyrimidin-2-yl)-benzoate
2-cyano-4-pentylphenyl 4-(5-hexylpyrimidin-2-yl)-benzoate
2-cyano-4-hexylphenyl 4-(5-hexylpyrimidin-2-yl)-benzoate
2-cyano-4-heptylphenyl 4-(5-hexylpyrimidin-2-yl)-benzoate
2-cyano-4-octylphenyl 4-(5-hexylpyrimidin-2-yl)-benzoate
2-cyano-4-nonylphenyl 4-(5-hexylpyrimidin-2-yl)-benzoate
2-cyano-4-decylphenyl 4-(5-hexylpyrimidin-2-yl)-benzoate 2-cyano-4-propylphenyl 4-(5-heptylpyrimidin-2-yl)-benzoate
2-cyano-4-pentylphenyl 4-(5-heptylpyrimidin-2-yl)-benzoate
2-cyano-4-hexylphenyl 4-(5-heptylpyrimidin-2-yl)-benzoate
2-cyano-4-heptylphenyl 4-(5-heptylpyrimidin-2-yl)-benzoate
2-cyano-4-octylphenyl 4-(5-heptylpyrimidin-2-yl)-benzoate
2-cyano-4-nonylphenyl 4-(5-heptylpyrimidin-2-yl)-benzoate
2-cyano-4-decylphenyl 4-(5-heptylpyrimidin-2-yl)-benzoate 2-cyano-4-propylphenyl 4-(5-octylpyrimidin-2-yl)-benzoate
2-cyano-4-pentylphenyl 4-(5-octylpyrimidin-2-yl)-benzoate
2-cyano-4-hexylphenyl 4-(5-octylpyrimidin-2-yl)-benzoate
2-cyano-4-heptylphenyl 4-(5-octylpyrimidin-2-yl)-benzoate
2-cyano-4-octylphenyl 4-(5-octylpyrimidin-2-yl)-benzoate
2-cyano-4-nonylphenyl 4-(5-octylpyrimidin-2-yl)-benzoate
2-cyano-4-decylphenyl 4-(5-octylpyrimidin-2-yl)-benzoate 2-cyano-4-propylphenyl 4-(5-nonylpyrimidin-2-yl)-benzoate
2-cyano-4-pentylphenyl 4-(5-nonylpyrimidin-2-yl)-benzoate
2-cyano-4-hexylphenyl 4-(5-nonylpyrimidin-2-yl)-benzoate
2-cyano-4-heptylphenyl 4-(5-nonylpyrimidin-2-yl)-benzoate
2-cyano-4-octylphenyl 4-(5-nonylpyrimidin-2-yl)-benzoate
2-cyano-4-nonylphenyl 4-(5-nonylpyrimidin-2-yl)-benzoate
2-cyano-4-decylphenyl 4-(5-nonylpyrimidin-2-yl)-benzoate 2-cyano-4-propylphenyl 4-(5-decylpyrimidin-2-yl)-benzoate
2-cyano-4-pentylphenyl 4-(5-decylpyrimidin-2-yl)-benzoate
2-cyano-4-hexylphenyl 4-(5-decylpyrimidin-2-yl)-benzoate
2-cyano-4-heptylphenyl 4-(5-decylpyrimidin-2-yl)-benzoate
2-cyano-4-octylphenyl 4-(5-decylpyrimidin-2-yl)-benzoate
2-cyano-4-nonylphenyl 4-(5-decylpyrimidin-2-yl)-benzoate
2-cyano-4-decylphenyl 4-(5-decylpyrimidin-2-yl)-benzoate

EXAMPLE 4

23.4 g of 4-octylbenzoic acid are converted into the acid chloride according to Example 1 using 15 g of thionyl chloride. The crude product is taken up in 350 ml of dichloromethane, 20 ml of triethylamine and 30.0 g of 2-fluoro-4-(5-octylpyrimidin-2-yl)-phenol (can be obtained from 3-fluoro-4-hydroxybenzamidine hydrochloride and methyl α-octyl-β-hydroxyacrylate) are added, and the mixture is refluxed for 8 hours. The reaction mixture is washed with ice water, dried over sodium sulfate and freed of solvent under reduced pressure. 3-Fluoro-4-(5-octylpyrimidin-2-yl)-phenyl 4-octylbenzoate remains.

The following are obtained analogously:

3-fluoro-4-(5-propylpyrimidin-2-yl)-phenyol 4-butylbenzoate
3-fluoro-4-(5-pentylpyrimidin-2-yl)-phenyl 4-butylbenzoate
3-fluoro-4-(5-hexylpyrimidin-2-yl)-phenyl 4-butylbenzoate
3-fluoro-4-(5-heptylpyrimidin-2-yl)-phenyl 4-butylbenzoate
3-fluoro-4-(5-octylpyrimidin-2-yl)-phenyl 4-butylbenzoate
3-fluoro-4-(5-nonylpyrimidin-2-yl)-phenyl 4-butylbenzoate
3-fluoro-4-(5-decylpyrimidin-2-yl)-phenyl 4-butylbenzoate 3-fluoro-4-(5-propylpyrimidin-2-yl)-phenyl 4-pentylbenzoate
3-fluoro-4-(5-pentylpyrimidin-2-yl)-phenyl 4-pentylbenzoate 3-fluoro-4-(5-hexylpyrimidin-2-yl)-phenyl 4-pentylbenzoate
3-fluoro-4-(5-heptylpyrimidin-2-yl)-phenyl 4-pentylbenzoate
3-fluoro-4-(5-octylpyrimidin-2-yl)-phenyl 4-pentylbenzoate
3-fluoro-4-(5-nonylpyrimidin-2-yl)-phenyl 4-pentylbenzoate
3-fluoro-4-(5-decylpyrimidin-2-yl)-phenyl 4-pentylbenzoate 3-fluoro-4-(5-propylpyrimidin-2-yl)-phenyl 4-hexylbenzoate
3-fluoro-4-(5-pentylpyrimidin-2-yl)-phenyl 4-hexylbenzoate
3-fluoro-4-(5-hexylpyrimidin-2-yl)-phenyl 4-hexylbenzoate
3-fluoro-4-(5-heptylpyrimidin-2-yl)-phenyl 4-hexylbenzoate
3-fluoro-4-(5-octylpyrimidin-2-yl)-phenyl 4-hexylbenzoate
3-fluoro-4-(5-nonylpyrimidin-2-yl)-phenyl 4-hexylbenzoate
3-fluoro-4-(5-decylpyrimidin-2-yl)-phenyl 4-hexylbenzoate 3-fluoro-4-(5-propylpyrimidin-2-yl)-phenyl 4-heptylbenzoate
3-fluoro-4-(5-pentylpyrimidin-2-yl)-phenyl 4-heptylbenzoate
3-fluoro-4-(5-hexylpyrimidin-2-yl)-phenyl 4-heptylbenzoate
3-fluoro-4-(5-heptylpyrimidin-2-yl)-phenyl 4-heptylbenzoate
3-fluoro-4-(5-octylpyrimidin-2-yl)-phenyl 4-heptylbenzoate
3-fluoro-4-(5-nonylpyrimidin-2-yl)-phenyl 4-heptylbenzoate
3-fluoro-4-(5-decylpyrimidin-2-yl)-phenyl 4-heptylbenzoate 3-fluoro-4-(5-propylpyrimidin-2-yl)-phenyl 4-octylbenzoate
3-fluoro-4-(5-pentylpyrimidin-2-yl)-phenyl 4-octylbenzoate
3-fluoro-4-(5-hexylpyrimidin-2-yl)-phenyl 4-octylbenzoate
3-fluoro-4-(5-heptylpyrimidin-2-yl)-phenyl 4-octylbenzoate
3-fluoro-4-(5-octylpyrimidin-2-yl)-phenyl 4-octylbenzoate
3-fluoro-4-(5-nonylpyrimidin-2-yl)-phenyl 4-octylbenzoate
3-fluoro-4-(5-decylpyrimidin-2-yl)-phenyl 4-octylbenzoate 3-fluoro-4-(5-propylpyrimidin-2-yl)-phenyl 4-nonylbenzoate
3-fluoro-4-(5-pentylpyrimidin-2-yl)-phenyl 4-nonylbenzoate
3-fluoro-4-(5-hexylpyrimidin-2-yl)-phenyl 4-nonylbenzoate
3-fluoro-4-(5-heptylpyrimidin-2-yl)-phenyl 4-nonylbenzoate
3-fluoro-4-(5-octylpyrimidin-2-yl)-phenyl 4-nonylbenzoate
3-fluoro-4-(5-nonylpyrimidin-2-yl)-phenyl 4-nonylbenzoate
3-fluoro-4-(5-decylpyrimidin-2-yl)-phenyl 4-nonylbenzoate 3-fluoro-4-(5-propylpyrimidin-2-yl)-phenyl 4-decylbenzoate
3-fluoro-4-(5-pentylpyrimidin-2-yl)-phenyl 4-decylbenzoate
3-fluoro-4-(5-hexylpyrimidin-2-yl)-phenyl 4-decylbenzoate
3-fluoro-4-(5-heptylpyrimidin-2-yl)-phenyl 4-decylbenzoate
3-fluoro-4-(5-octylpyrimidin-2-yl)-phenyl 4-decylbenzoate
3-fluoro-4-(5-nonylpyrimidin-2-yl)-phenyl 4-decylbenzoate
3-fluoro-4-(5-decylpyrimidin-2-yl)-phenyl 4-decylbenzoate

EXAMPLE 5

17.0 g of 4-(5-decylpyrimidin-2-yl)-benzoic acid (obtained from 4-(5-decylpyrimidin-2-yl)-benzonitrile by saponification), 10.4 g of 3-fluoro-4-octylphenol and 10.5 g of dicyclohexylcarbodiimide are stirred for 14 hours at 20° in 280 ml of dichloromethane. The precipitated dicyclohexylurea is filtered off and the solvent is stripped to a small volume, whereupon 3-fluoro-4-octylphenyl 4-(5-decylpyrimidin-2-yl)-benzoate crystallizes.

The following are obtained analogously:

3-fluoro-4-propylphenyl 4-(5-butylpyrimidin-2-yl)-benzoate
3-fluoro-4-pentylphenyl 4-(5-butylpyrimidin-2-yl)-benzoate
3-fluoro-4-hexylphenyl 4-(5-butylpyrimidin-2-yl)-benzoate
3-fluoro-4-heptylphenyl 4-(5-butylpyrimidin-2-yl)-benzoate
3-fluoro-4-octylphenyl 4-(5-butylpyrimidin-2-yl)-benzoate
3-fluoro-4-nonylphenyl 4-(5-butylpyrimidin-2-yl)-benzoate
3-fluoro-4-decylphenyl 4-(5-butylpyrimidin-2-yl)-benzoate 3-fluoro-4-propylphenyl 4-(5-pentylpyrimidin-2-yl)-benzoate
3-fluoro-4-pentylphenyl 4-(5-pentylpyrimidin-2-yl)-benzoate
3-fluoro-4-hexylphenyl 4-(5-pentylpyrimidin-2-yl)-benzoate
3-fluoro-4-heptylphenyl 4-(5-pentylpyrimidin-2-yl)-benzoate
3-fluoro-4-octylphenyl 4-(5-pentylpyrimidin-2-yl)-benzoate
3-fluoro-4-nonylphenyl 4-(5-pentylpyrimidin-2-yl)-benzoate
3-fluoro-4-decylphenyl 4-(5-pentylpyrimidin-2-yl)-benzoate 3-fluoro-4-propylphenyl 4-(5-hexylpyrimidin-2-yl)-benzoate
3-fluoro-4-pentylphenyl 4-(5-hexylpyrimidin-2-yl)-benzoate
3-fluoro-4-hexylphenyl 4-(5-hexylpyrimidin-2-yl)-benzoate
3-fluoro-4-heptylphenyl 4-(5-hexylpyrimidin-2-yl)-benzoate 3-fluoro-4-octylphenyl 4-(5-hexylpyrimidin-2-yl)-benzoate
3-fluoro-4-nonylphenyl 4-(5-hexylpyrimidin-2-yl)-benzoate
3-fluoro-4-decylphenyl 4-(5-hexylpyrimidin-2-yl)-benzoate 3-fluoro-4-propylphenyl 4-(5-heptylpyrimidin-2-yl)-benzoate
3-fluoro-4-pentylphenyl 4-(5-heptylpyrimidin-2-yl)-benzoate
3-fluoro-4-hexylphenyl 4-(5-heptylpyrimidin-2-yl)-benzoate
3-fluoro-4-heptylphenyl 4-(5-heptylpyrimidin-2-yl)-benzoate
3-fluoro-4-octylphenyl 4-(5-heptylpyrimidin-2-yl)-benzoate
3-fluoro-4-nonylphenyl 4-(5-heptylpyrimidin-2-yl)-benzoate
3-fluoro-4-decylphenyl 4-(5-heptylpyrimidin-2-yl)-benzoate 3-fluoro-4-propylphenyl 4-(5-octylpyrimidin-2-yl)-benzoate
3-fluoro-4-pentylphenyl 4-(5-octylpyrimidin-2-yl)-benzoate
3-fluoro-4-hexylphenyl 4-(5-octylpyrimidin-2-yl)-benzoate
3-fluoro-4-heptylphenyl 4-(5-octylpyrimidin-2-yl)-benzoate
3-fluoro-4-octylphenyl 4-(5-octylpyrimidin-2-yl)-benzoate
3-fluoro-4-nonylphenyl 4-(5-octylpyrimidin-2-yl)-benzoate
3-fluoro-4-decylphenyl 4-(5-octylpyrimidin-2-yl)-benzoate 3-fluoro-4-propylphenyl 4-(5-nonylpyrimidin-2-yl)-benzoate
3-fluoro-4-pentylphenyl 4-(5-nonylpyrimidin-2-yl)-benzoate
3-fluoro-4-hexylphenyl 4-(5-nonylpyrimidin-2-yl)-benzoate
3-fluoro-4-heptylphenyl 4-(5-nonylpyrimidin-2-yl)-benzoate
3-fluoro-4-octylphenyl 4-(5-nOnylpyrimidin-2-yl)-benzoate
3-fluoro-4-nonylphenyl 4-(5-nonylpyrimidin-2-yl)-benzoate
3-fluoro-4-decylphenyl 4-(5-nonylpyrimidin-2-yl)-benzoate 3-fluoro-4-propylphenyl 4-(5-decylpyrimidin-2-yl)-benzoate
3-fluoro-4-pentylphenyl 4-(5-decylpyrimidin-2-yl)-benzoate
3-fluoro-4-hexylphenyl 4-(5-decylpyrimidin-2-yl)-benzoate
3-fluoro-4-heptylphenyl 4-(5-decylpyrimidin-2-yl)-benzoate
3-fluoro-4-octylphenyl 4-(5-decylpyrimidin-2-yl)-benzoate
3-fluoro-4-nonylphenyl 4-(5-decylpyrimidin-2-yl)-benzoate
3-fluoro-4-decylphenyl 4-(5-decylpyrimidin-2-yl)-benzoate

EXAMPLE 6

2.6 g of 2-fluoro-4-n-hexyloxybenzoyl chloride (can be obtained by alkylation of 3-fluoro-4-cyanophenol using 1-bromohexane, alkaline saponification of the nitrile to the acid and conversion of the latter into its chloride by heating with thionyl chloride), 2.7 g of 5-hydroxyl-2-(4-heptylphenyl)-pyrimidine (prepared according to Example 18) and 0.8 g of pyridine are heated for 3 hours at 100° in 20 ml of toluene. After cooling, the pyridine hydrochloride is filtered off under suction, and the filtrate is washed with water until neutral and dried. Removal of the solvent by distillation and crystallization from isopropanol give 2-(4-heptylphenyl)-pyrimidin-5-yl 2-fluoro-4-hexyloxybenzoate.

The following are obtained analogously:

2-(4-propylphenyl)-pyrimidin-5-yl 2-fluoro-4-propyloxybenzoate
2-(4-pentylphenyl)-pyrimidin-5-yl 2-fluoro-4-propyloxybenzoate
2-(4-hexylphenyl)-pyrimidin-5-yl 2-fluoro-4-propyloxybenzoate
2-(4-heptylphenyl)-pyrimidin-5-yl 2-fluoro-4-propyloxybenzoate
2-(4-octylphenyl)-pyrimidin-5-yl 2-fluoro-4-propyloxybenzoate
2-(4-nonylphenyl)-pyrimidin-5-yl 2-fluoro-4-propyloxybenzoate
2-(4-decylphenyl)-pyrimidin-5-yl 2-fluoro-4-propyloxybenzoate 2-(4-propylphenyl)-pyrimidin-5-yl 2-fluoro-4-pentyloxybenzoate
2-(4-pentylphenyl)-pyrimidin-5-yl 2-fluoro-4-pentyloxybenzoate
2-(4-hexylphenyl)-pyrimidin-5-yl 2-fluoro-4-pentyloxybenzoate
2-(4-heptylphenyl)-pyrimidin-5-yl 2-fluoro-4-pentyloxybenzoate
2-(4-octylphenyl)-pyrimidin-5-yl 2-fluoro-4-pentyloxybenzoate
2-(4-nonylphenyl)-pyrimidin-5-yl 2-fluoro-4-pentyloxybenzoate
2-(4-decylphenyl)-pyrimidin-5-yl 2-fluoro-4-pentyloxybenzoate 2-(4-propylphenyl)-pyrimidin-5-yl 2-fluoro-4-hexyloxybenzoate
2-(4-pentylphenyl)-pyrimidin-5-yl 2-fluoro-4-hexyloxybenzoate
2-(4-hexylphenyl)-pyrimidin-5-yl 2-fluoro-4-hexyloxybenzoate
2-(4-heptylphenyl)-pyrimidin-5-yl 2-fluoro-4-hexyloxybenzoate
2-(4-octylphenyl)-pyrimidin-5-yl 2-fluoro-4-hexyloxybenzoate
2-(4-nonylphenyl)-pyrimidin-5-yl 2-fluoro-4-hexyloxybenzoate
2-(4-decylphenyl)-pyrimidin-5-yl 2-fluoro-4-hexyloxybenzoate 2-(4-propylphenyl)-pyrimidin-5-yl 2-fluoro-4-heptyloxybenzoate
2-(4-pentylphenyl)-pyrimidin-5-yl 2-fluoro-4-heptyloxybenzoate
2-(4-hexylphenyl)-pyrimidin-5-yl 2-fluoro-4-heptyloxybenzoate 2-(4-heptylphenyl)-pyrimidin-5-yl 2-fluoro-4-heptyloxybenzoate
2-(4-octylphenyl)-pyrimidin-5-yl 2-fluoro-4-heptyloxybenzoate
2-(4-nonylphenyl)-pyrimidin-5-yl 2-fluoro-4-heptyloxybenzoate
2-(4-decylphenyl)-pyrimidin-5-yl 2-fluoro-4-heptyloxybenzoate 2-(4-propylphenyl)-pyrimidin-5-yl 2-fluoro-4-octyloxybenzoate
2-(4-pentylphenyl)-pyrimidin-5-yl 2-fluoro-4-octyloxybenzoate
2-(4-hexylphenyl)-pyrimidin-5-yl 2-fluoro-4-octyloxybenzoate
2-(4-heptylphenyl)-pyrimidin-5-yl 2-fluoro-4-octyloxybenzoate
2-(4-octylphenyl)-pyrimidin-5-yl 2-fluoro-4-octyloxybenzoate
2-(4-nonylphenyl)-pyrimidin-5-yl 2-fluoro-4-octyloxybenzoate
2-(4-decylphenyl)-pyrimidin-5-yl 2-fluoro-4-octyloxybenzoate 2-(4-propylphenyl)-pyrimidin-5-yl 2-fluoro-4-nonyloxybenzoate
2-(4-pentylphenyl)-pyrimidin-5-yl 2-fluoro-4-nonyloxybenzoate
2-(4-hexylphenyl)-pyrimidin-5-yl 2-fluoro-4-nonyloxybenzoate
2-(4-heptylphenyl)-pyrimidin-5-yl 2-fluoro-4-nonyloxybenzoate
2-(4-octylphenyl)-pyrimidin-5-yl 2-fluoro-4-nonyloxybenzoate
2-(4-nonylphenyl)-pyrimidin-5-yl 2-fluoro-4-nonyloxybenzoate
2-(4-decylphenyl)-pyrimidin-5-yl 2-fluoro-4-nonyloxybenzoate 2-(4-propylphenyl)-pyrimidin-5-yl 2-fluoro-4-decyloxybenzoate
2-(4-pentylphenyl)-pyrimidin-5-yl 2-fluoro-4-decyloxybenzoate
2-(4-hexylphenyl)-pyrimidin-5-yl 2-fluoro-4-decyloxybenzoate
2-(4-heptylphenyl)-pyrimidin-5-yl 2-fluoro-4-decyloxybenzoate
2-(4-octylphenyl)-pyrimidin-5-yl 2-fluoro-4-decyloxybenzoate
2-(4-nonylphenyl)-pyrimidin-5-yl 2-fluoro-4-decyloxybenzoate
2-(4-decylphenyl)-pyrimidin-5-yl 2-fluoro-4-decyloxybenzoate

EXAMPLE 7

The acid chloride, prepared analogously to Example 20 from 29.8 g of 4-(5-heptylpyrimidin-2-yl)-benzoic acid using 15 g of thionyl chloride, is stirred for 12 hours at 20° in 330 ml of dichloromethane after addition of 27.2 g of 2,3-dicyano-4-octyloxyphenol (obtained from 2,3-dicyanohydroquinone and one equivalent of octyl bromide in DMF in the presence of potassium carbonate) and 20 ml of triethylamine. The mixture is subsequently washed with ice water, dried over sodium sulfate and freed of solvent under reduced pressure. 2,3-Dicyano-4-octyloxyphenyl 4-(5-heptylpyrimidin-2-yl)-benzoate is thus obtained.

The following are obtained analogously:

2,3-dicyano-4-propyloxyphenyl 4-(5-propylpyrimidin-2-yl)-benzoate
2,3-dicyano-4-hexyloxyphenyl 4-(5-propylpyrimidin-2-yl)-benzoate
2,3-dicyano-4-heptyloxyphenyl 4-(5-propylpyrimidin-2-yl)-benzoate
2,3-dicyano-4-octyloxyphenyl 4-(5-propylpyrimidin-2-yl)-benzoate
2,3-dicyano-4-nonyloxyphenyl 4-(5-propylpyrimidin-2-yl)-benzoate
2,3-dicyano-4-decyloxyphenyl 4-(5-propylpyrimidin-2-yl)-benzoate 2,3-dicyano-4-propyloxyphenyl 4-(5-pentylpyrimidin-2-yl)-benzoate
2,3-dicyano-4-hexyloxyphenyl 4-(5-pentylpyrimidin-2-yl)-benzoate
2,3-dicyano-4-heptyloxyphenyl 4-(5-pentylpyrimidin-2-yl)-benzoate
2,3-dicyano-4-octyloxyphenyl 4-(5-pentylpyrimidin-2-yl)-benzoate
2,3-dicyano-4-nonyloxyphenyl 4-(5-pentylpyrimidin-2-yl)-benzoate
2,3-dicyano-4-decyloxyphenyl 4-(5-pentylpyrimidin-2-yl)-benzoate 2,3-dicyano-4-hexyloxyphenyl 4-(5-hexylpyrimidin-2-yl)-benzoate
2,3-dicyano-4-heptyloxyphenyl 4-(5-hexylpyrimidin-2-yl)-benzoate
2,3-dicyano-4-octyloxyphenyl 4-(5-hexylpyrimidin-2-yl)-benzoate
2,3-dicyano-4-nonyloxyphenyl 4-(5-hexylpyrimidin-2-yl)-benzoate
2,3-dicyano-4-decyloxyphenyl 4-(5-hexylpyrimidin-2yl)-benzoate 2,3-dicyano-4-propyloxyphenyl 4-(5-heptylpyrimidin-2-yl)-benzoate
2,3-dicyano-4-pentyloxyphenyl 4-(5-heptylpyrimidin-2-yl)-benzoate
2,3-dicyano-4-hexyloxyphenyl 4-(5-heptylpyrimidin-2-yl)-benzoate
2,3-dicyano-4-octyloxyphenyl 4-(5-heptylpyrimidin-2-yl)-benzoate
2,3-dicyano-4-nonyloxyphenyl 4-(5-heptylpyrimidin-2-yl)-benzoate
2,3-dicyano-4-decyloxyphenyl 4-(5-heptylpyrimidin-2-yl)-benzoate 2,3-dicyano-4-propyloxyphenyl 4-(5-octylpyrimidin-2-yl)-benzoate
2,3-dicyano-4-pentyloxyphenyl 4-(5-octylpyrimidin-2-yl)-benzoate
2,3-dicyano-4-hexyloxyphenyl 4-(5-octylpyrimidin-2-yl)-benzoate
2,3-dicyano-4-heptyloxyphenyl 4-(5-octylpyrimidin-2-yl)-benzoate
2,3-dicyano-4-octyloxyphenyl 4-(5-octylpyrimidin-2-yl)-benzoate
2,3-dicyano-4-nonyloxyphenyl 4-(5-octylpyrimidin-2-yl)-benzoate
2,3-dicyano-4-decyloxyphenyl 4-(5-octylpyrimidin-2-yl)-benzoate 2,3-dicyano-4-propyloxyphenyl 4-(5-nonylpyrimidin-2-yl)-benzoate 2,3-dicyano-4-pentyloxyphenyl 4-(5-nonylpyrimidin-2-yl)-benzoate
2,3-dicyano-4-hexyloxyphenyl 4-(5-nonylpyrimidin-2-yl)-benzoate
2,3-dicyano-4-heptyloxyphenyl 4-(5-nonylpyrimidin-2-yl)-benzoate
2,3-dicyano-4-octyloxyphenyl 4-(5-nonylpyrimidin-2-yl)-benzoate
2,3-dicyano-4-nonyloxyphenyl 4-(5-nonylpyrimidin-2-yl)-benzoate
2,3-dicyano-4-decyloxyphenyl 4-(5-nonylpyrimidin-2-yl)-benzoate 2,3-dicyano-4-propyloxyphenyl 4-(5-decylpyrimidin-2-yl)-benzoate
2,3-dicyano-4-pentyloxyphenyl 4-(5-decylpyrimidin-2-yl)-benzoate
2,3-dicyano-4-hexyloxyphenyl 4-(5-decylpyrimidin-2-yl)-benzoate
2,3-dicyano-4-heptyloxyphenyl 4-(5-decylpyrimidin-2-yl)-benzoate
2,3-dicyano-4-octyloxyphenyl 4-(5-decylpyrimidin-2-yl)-benzoate
2,3-dicyano-4-nonyloxyphenyl 4-(5-decylpyrimidin-2-yl)-benzoate
2,3-dicyano-4-decyloxyphenyl 4-(5-decylpyrimidin-2-yl)-benzoate

EXAMPLE 8

7.9 g of 2-fluoro-4-(5-n-heptylpyrimidin-2-yl)-benzoic acid (can be obtained by alkaline saponification of 2-(3-fluoro-4-cyanophenyl)-5-n-heptylpyrimidine) are suspended in 80 ml of dichloromethane. 4.3 g of trans-4-n-pentylcyclohexanol and 0.3 g of 4-(dimethylamino)pyridine are added and 5.8 g of dicyclohexylcarbodiimide are added with stirring at 5°–10°. The mixture is stirred for a further 30 minutes, with cooling, then overnight at room temperature, the precipitated urea is filtered off, and the filtrate is concentrated to a residue. Recrystallization from ethanol gives trans-4-n-pentylcyclohexyl 2-fluoro-4-(5n-heptylpyrimidin-2-yl)-benzoate.

The following are obtained analogously:

trans-4-propylcyclohexyl 2-fluoro-4-(5-butylpyrimidin-2-yl)-benzoate
trans-4-pentylcyclohexyl 2-fluoro-4-(5-butylpyrimidin-2-yl)-benzoate
trans-4-hexylcyclohexyl 2-fluoro-4-(5-butylpyrimidin-2-yl)-benzoate
trans-4-heptylcyclohexyl 2-fluoro-4-(5-butylpyrimidin-2-yl)-benzoate
trans-4-octylcyclohexyl 2-fluoro-4-(5-butylpyrimidin-2-yl)-benzoate
trans-4-nonylcyclohexyl 2-fluoro-4-(5-butylpyrimidin-2-yl)-benzoate
trans-4-decylcyclohexyl 2-fluoro-4-(5-butylpyrimidin-2-yl)-benzoate trans-4-propylcyclohexyl 2-fluoro-4-(5-pentylpyrimidin-2-yl)-benzoate
trans-4-pentylcyclohexyl 2-fluoro-4-(5-pentylpyrimidin-2-yl)-benzoate
trans-4-hexylcyclohexyl 2-fluoro-4-(5-pentylpyrimidin-2-yl)-benzoate
trans-4-heptylcyclohexyl 2-fluoro-4-(5-pentylpyrimidin-2-yl)-benzoate
trans-4-octylcyclohexyl 2-fluoro-4-(5-pentylpyrimidin-2-yl)-benzoate
trans-4-nonylcyclohexyl 2-fluoro-4-(5-pentylpyrimidin-2-yl)-benzoate
trans-4-decylcyclohexyl 2-fluoro-4-(5-pentylpyrimidin-2-yl)-benzoate trans-4-propylcyclohexyl 2-fluoro-4-(5-hexylpyrimidin-2-yl)-benzoate, C 77° N 117° I
trans-4-pentylcyclohexyl 2-fluoro-4-(5-hexylpyrimidin-2-yl)-benzoate
trans-4-hexylcyclohexyl 2-fluoro-4-(5-hexylpyrimidin-2-yl)-benzoate
trans-4-heptylcyclohexyl 2-fluoro-4-(5-hexylpyrimidin-2-yl)-benzoate
trans-4-octylcyclohexyl 2-fluoro-4-(5-hexylpyrimidin-2-yl)-benzoate
trans-4-nonylcyclohexyl 2-fluoro-4-(5-hexylpyrimidin-2-yl)-benzoate
trans-4-decylcyclohexyl 2-fluoro-4-(5-hexylpyrimidin-2-yl)-benzoate trans-4-propylcyclohexyl 2-fluoro-4-(5-heptylpyrimidin-2-yl)-benzoate, C 61° $S_A$ (49°) N 120° I
trans-4-pentylcyclohexyl 2-fluoro-4-(5-heptylpyrimidin-2-yl)-benzoate
trans-4-hexylcyclohexyl 2-fluoro-4-(5-heptylpyrimidin-2-yl)-benzoate
trans-4-heptylcyclohexyl 2-fluoro-4-(5-heptylpyrimidin-2-yl)-benzoate
trans-4-octylcyclohexyl 2-fluoro-4-(5-heptylpyrimidin-2-yl)-benzoate
trans-4-nonylcyclohexyl 2-fluoro-4-(5-heptylpyrimidin-2-yl)-benzoate
trans-4-decylcyclohexyl 2-fluoro-4-(5-heptylpyrimidin-2-yl)-benzoate trans-4-propylcyclohexyl 2-fluoro-4-(5-octylpyrimidin-2-yl)-benzoate
trans-4-pentylcyclohexyl 2-fluoro-4-(5-octylpyrimidin-2-yl)-benzoate
trans-4-hexylcyclohexyl 2-fluoro-4-(5-octylpyrimidin-2-yl)-benzoate
trans-4-octylcyclohexyl 2-fluoro-4-(5-octylpyrimidin-2-yl)-benzoate
trans-4-nonylcyclohexyl 2-fluoro-4-(5-octylpyrimidin-2-yl)-benzoate
trans-4-decylcyclohexyl 2-fluoro-4-(5-octylpyrimidin-2-yl)-benzoate trans-4-propylcyclohexyl 2-fluoro-4-(5-nonylpyrimidin-2-yl)-benzoate
trans-4-pentylcyclohexyl 2-fluoro-4-(5-nonylpyrimidin-2-yl)-benzoate
trans-4-hexylcyclohexyl 2-fluoro-4-(5-nonylpyrimidin-2-yl)-benzoate
trans-4-heptylcyclohexyl 2-fluoro-4-(5-nonylpyrimidin-2-yl)-benzoate
trans-4-octylcyclohexyl 2-fluoro-4-(5-nonylpyrimidin-2-yl)-benzoate
trans-4-nonylcyclohexyl 2-fluoro-4-(5-nonylpyrimidin-2-yl)-benzoate
trans-4-decylcyclohexyl 2-fluoro-4-(5-nonylpyrimidin-2-yl)-benzoate trans-4-propylcyclohexyl 2-fluoro-4-(5-decylpyrimidin-2-yl)-benzoate
trans-4-pentylcyclohexyl 2-fluoro-4-(5-decylpyrimidin-2-yl)-benzoate trans-4-hexylcyclohexyl 2-fluoro-4-(5-decylpyrimidin-2-yl)-benzoate trans-4-octylcyclohexyl 2-fluoro-4-(5-decylpyrimidin-2-yl)-benzoate trans-4-nonylcyclohexyl 2-fluoro-4-(5-decylpyrimidin-2-yl)-benzoate trans-4-decylcyclohexyl 2-fluoro-4-(5-decylpyrimidin-2-yl)-benzoate

EXAMPLE 9

4-(5-Nonylpyrimidin-2-yl)-phenyl 4-(trans-4-pentylcyclohexyl)-3-fluorobenzoate, C 112° N 247° I, is obtained according to Example 1 from 4-(trans-4-pentylcyclohexyl)-3-fluorobenzoic acid and 4-(5-nonylpyrimidin-2-yl)-phenol.

The following are prepared analogously:

4-(5-nonylpyrimidin-2-yl)-phenyl 4-trans-4-propylcyclohexyl)-3-fluorobenzoate 4-(5-nonylpyrimidin-2-yl)-phenyl 4-trans-4-hexylcyclohexyl)-3-fluorobenzoate 4-(5-nonylpyrimidin-2-yl)-phenyl 4-trans-4-heptylcyclohexyl)-3-fluorobenzoate 4-(5-nonylpyrimidin-2-yl)-phenyl 4-trans-4-octylcyclohexyl)-3-fluorobenzoate 4-(5-nonylpyrimidin-2-yl)-phenyl 4-trans-4-nonylcyclohexyl)-3-fluorobenzoate 4-(5-nonylpyrimidin-2-yl)-phenyl 4-trans-4-decylcyclohexyl)-3-fluorobenzoate

EXAMPLE 10

A liquid-crystalline phase comprising
31% of 2-p-nonyloxyphenyl-5-nonylpyrimidine
9% of 2-p-decyloxyphenyl-5-octylpyrimidine
14% of 2-p-octyloxyphenyl-5-octylpyrimidine
18% of 2-p-nonyloxyphenyl-5-heptylpyrimidine
13% of 2-p-heptyloxyphenyl-5-heptylpyrimidine
10% of 4-(5-octylpyrimidin-2-yl)-phenyl 2-fluoro-4-decyloxybenzoate
5% of 4-(5-decylpyrimidin-2-yl)-phenyl 2-fluoro-4-hexyloxybenzoate has $C/S_c$ 7°, $S_c/S_A$ 57°, $S_A/N$ 67°, $N/I$ 70.5°.

EXAMPLE 11

A liquid-crystalline phase comprising
28% of 2-p-nonyloxyphenyl-5-nonylpyrimidine
3% of 2-p-nonyloxyphenyl-5-octylpyrimidine
25% of 2-p-heptyloxyphenyl-5-octylpyrimidine
10% of 2-p-heptyloxy-5-heptylpyrimidine
5% of 2-p-decyloxy-5-heptylpyrimidine
9% of 4-(5-octylpyrimidin-2-yl)-phenyl 2-fluoro-4-decyloxybenzoate
10% of 4-(5-heptylpyrimidin-2-yl)-phenyl 3-fluoro-4-heptyloxybenzoate
10% of 2-fluoro-4-nonylphenyl 4-(5-decylpyrimidin-2-yl)-benzoate has $C/S_c$ 13°, $S_c/S_A$ 64°, $S_A/N$ 68°, $N/I$ 83°.

EXAMPLE 12

A liquid-crystalline phase comprising
30% of 2-p-nonyloxyphenyl-5-nonylpyrimidine
15% of 2-p-decyloxyphenyl-5-octylpyrimidine
15% of 2-p-octyloxyphenyl-5-octylpyrimidine
12% of 2-p-nonyloxyphenyl-5-heptylpyrimidine
10% of 3-fluoro-4-hexylphenyl 4-(5-octylpyrimidin-2-yl)-benzoate
3% of 2-cyano-4-decylphenyl 4-(5-decylpyrimidin-2-yl)-benzoate
6% of 2-(4-heptylphenyl)-pyrimidin-5-yl 2-fluoro-4-heptyloxybenzoate
9% of 2-(4-octylphenyl)-pyrimidin-5-yl 3-fluoro-4-hexylbenzoate has $C/S_c$ 16°, $S_c/S_A$ 59°, $S_A/N$ 63°, $N/I$ 79°.

EXAMPLE 13

A liquid-crystalline phase comprising
30% of 2-p-nonyloxyphenyl-5-nonylpyrimidine
15% of 2-p-decyloxyphenyl-5-octylpyrimidine
20% of 2-p-octyloxyphenyl-5-octylpyrimidine
15% of 2-p-nonyloxyphenyl-5-heptylpyrimidine
10% of 2-p-heptyloxyphenyl-5-heptylpyrimidine
10% of 2-fluoro-4-(5-octylpyrimidin-2-yl)-phenyl 4-octylbenzoate has $C/S_c$ 4°, $S_c/S_A$ 22°, $S_A/N$ 65°, $N/I$ 74°.

EXAMPLE 14

A liquid-crystalline phase comprising
33% of 4-(5-hexylpyrimidin-2-yl)-phenyl p-hexylbenzyl ether
15% of 4-(5-heptylpyrimidin-2-yl)-phenyl p-pentylbenzyl ether
10% of 4-(5-hexylpyrimidin-2-yl)-phenyl p-pentylbenzyl ether
3% of 4-(5-nonylpyrimidin-2-yl)-phenyl p-hexylbenzyl ether
24% of 4-(5-heptylpyrimidin-2-yl)-phenyl p-hexylbenzyl ether
10% of 4-(5-octylpyrimidin-2-yl)-phenyl 2-fluoro-4-heptyloxybenzoate
5% of 3-fluoro-4-octylphenyl 4-(5-decylpyrimidin-2-yl)-benzoate has $C/S_c$ 3°, $S_c/N$ 75°, $N/I$ 98°.

EXAMPLE 15

A liquid-crystalline phase comprising
32% of 4-(5-hexylpyrimidin-2-yl)-phenyl p-hexylbenzyl ether
16% of 4-(5-heptylpyrimidin-2-yl)-phenyl p-pentylbenzyl ether
9% of 4-(5-hexylpyrimidin-2-yl)-phenyl p-pentylbenzyl ether
2% of 4-(5-nonylpyrimidin-2-yl)-phenyl p-hexylbenzyl ether
18% of 4-(5-nonylpyrimidin-2-yl)-phenyl p-pentylbenzyl ether
13% of 4-(5-heptylpyrimidin-2-yl)-phenyl 3-fluoro-4-heptyloxybenzoate
5% of 2-fluoro-4-nonylphenyl 4-(5-decylpyrimidin-2-yl)-benzoate
5% of 2-cyano-4-octylphenyl 4-(5-nonylpyrimidin-2-yl)-benzoate has $C/S_c$ −1°, $S_c/N$ 77°, $N/I$ 94°.

EXAMPLE 16

A liquid-crystalline phase comprising
17% of 4-(5-heptylpyrimidin-2-yl)-phenyl p-pentylbenzyl ether
25% of 4-(5-heptylpyrimidin-2-yl)-phenyl p-hexylbenzyl ether
13% of 4-(nonylpyrimidin-2-yl)-phenyl p-pentylbenzyl ether
4% of 4-(nonylpyrimidin-2-yl)-phenyl p-hexylbenzyl ether
11% of 2-(4-nonylphenyl)-pyrimidin-5-yl 2-fluoro-4-heptylbenzoate 10% of 2-fluoro-4-(5-decylpyrimidin-2-yl)-phenyl 4-octylbenzoate
15% of 4-(5-heptylpyrimidin-2-yl)-phenyl 2-fluoro-4-heptyloxybenzoate
5% of 2-fluoro-4-nonylphenyl 4-(5-nonylpyrimidin-2-yl)-benzoate
has C/S$_c$ 5°, S$_c$/N 75°, N/I 97°.

EXAMPLE 17

A liquid-crystalline phase comprising
33% of 4-(5-hexylpyrimidin-2-yl)-phenyl p-hexylbenzyl ether
18% of 4-(5-heptylpyrimidin-2-yl)-phenyl p-pentylbenzyl ether
10% of 4-(5-hexylpyrimidin-2-yl)-phenyl p-pentylbenzyl ether
3% of 4-(5-nonylpyrimidin-2-yl)-phenyl p-hexylbenzyl ether
25% of 4-(5-heptylpyrimidin-2-yl)-phenyl p-hexylbenzyl ether
4% of 5-(4-octylphenyl)-pyrimidin-2-yl 3-fluoro-4-octylbenzoate
7% of 2-fluoro-4-(5-decylpyrimidin-2-yl)-phenyl 4-heptylbenzoate
has C/S$_c$ 10°, S$_c$/N 77°, N/I 100°.

EXAMPLE 18

A liquid-crystalline phase comprising
50% of 4-(5-nonylpyrimidin-2-yl)-phenyl 3-chloro-4-(2-octyloxy)-benzoate and
50% of 4'-octyloxybiphenyl-4-yl 3-chloro-4-(2-octyloxy)-benzoate
exhibits S$_c$* 58° Ch 77° I and P$_s$=91 nC/cm$^2$ at 25°.

EXAMPLE 19

A liquid-crystalline phase comprising
10% of 4-(5-heptylpyrimidin-2-yl)-phenyl 3-bromo-4-octyloxybenzoate,
10% of 4-(5-nonylpyrimidin-2-yl)-phenyl 3-bromo-4-octylbenzoate,
20% of 4-(5-nonylpyrimidin-2-yl)-phenyl 3-bromo-4-octyloxybenzoate
40% of 4-(5-nonylpyrimidin-2-yl)-phenyl 3-cyano-4-octyloxybenzoate, and
20% of optically active 4-(5-nonylpyrimidin-2-yl)-phenyl 3-chloro-4-(2-octyloxy)-benzoate
exhibits S$_c$* 78° Ch 105° I.

EXAMPLE 20

A liquid-crystalline phase comprising
5% of 4-(5-heptylpyrimidin-2-yl)-phenyl 3-bromo-4-octyloxybenzoate
5% of 4-(5-nonylpyrimidin-2-yl)-phenyl 3-bromo-4-octylbenzoate
20% of 4-(5-nonylpyrimidin-2-yl)-phenyl 3-bromo-4-octyloxybenzoate,
40% of 4-(5-nonylpyrimidin-2-yl)-phenyl 3-cyano-4-octyloxybenzoate,
20% of optically active 4-(5-nonylpyrimidin-2-yl)-phenyl 3-chloro-4-(2-octyloxy)-benzoate and
10% of trans-4-propylcyclohexyl 2-fluoro-4-(5-heptylpyrimidin-2-yl)-benzoate
exhibits S$_c$* 71° S$_A$* 74° Ch 97° I.

EXAMPLE 21

A liquid-crystalline phase comprising
11% of p-(5-heptylpyrimidin-2-yl)-phenyl p-pentylbenzyl ether,
15% of p-(5-heptylpyrimidin-2-yl)-phenyl p-hexylbenzyl ether,
18% of p-(5-nonylpyrimidin-2-yl)-phenyl p-pentylbenzyl ether,
14% of p-(5-nonylpyrimidin-2-yl)-phenyl p-heptylbenzyl ether,
23% of 2-p-nonyloxyphenyl-5-nonylpyrimidine,
5% of 4-(5-heptylpyrimidin-2-yl)-phenyl p-hexyloxybenzoate,
4% of 4-(5-octylpyrimidin-2-yl)-phenyl p-octyloxy-m-fluorobenzoate and
10% of R-4-(5-hexylpyrimidin-2-yl)-phenyl 2-chloropropionate
exhibits C 4° S$_c$* 76° Ch 95° I.

EXAMPLE 22

A liquid-crystalline phase comprising
3% of 2-p-hexyloxyphenyl-5-heptylpyrimidine,
3% of 2-p-heptyloxyphenyl-5-heptylpyrimidine,
3% of 2-p-octyloxyphenyl-5-hepthylpyrimidine,
3% of 2-p-nonyloxyphenyl-5-heptylpyrimidine,
6% of 2-p-hexyloxyphenyl-5-nonylpyrimidine,
15% of 2-p-nonyloxyphenyl-5-nonylpyrimidine,
16% of 1-(p-hexylphenyl)-2-(p-(5-heptylpyrimidin-2-yl)-phenyl)-ethane
19% of 1-(p-octyl-m-fluorophenyl)-2-(p-(5-octyl-pyrimidin-2-yl)-phenyl)-ethane
15% of optically active 4-(5-nonylpyrimidin-2-yl)-phenyl 3-chloro-4-(2-octyloxy)-benzoate and
17% of optically active 1-p-(2-octyloxycarbonyl)-phenyl-2-(p-(5-heptylpyrimidin-2-yl)-phenyl)-ethane
exhibits C 9° S$_c$* 74° Ch 89° I.

EXAMPLE 23

A liquid-crystalline phase comprising
4% of 2-p-heptyloxyphenyl-5-octylpyrimidine,
4% of 2-o-octyloxyphenyl-5-octylpyrimidine,
4% of 2-p-nonyloxyphenyl-5-octylpyrimidine,
16% of p-(5-nonylpyrimidin-2-yl)-phenyl p-pentylbenzyl ether,
11% of p-(5-nonylpyrimidin-2-yl)-phenyl p-heptylbenzyl ether,
13% of 5-(p-octylphenyl)-pyrimidin-2-yl p-octyloxybenzoate,
16% of 5-(p-heptylphenyl)-pyrimidin-2-yl p-hexyloxybenzoate,
11% of 5-(p-octylphenyl)-pyrimidin-2-yl p-heptyloxy-m-fluorobenzoate and
21% of 2-p-nonyloxyphenyl-5-nonylpyrimidine
exhibits C 5° S$_c$.

EXAMPLE 24

A liquid-crystalline phase comprising
11% of p-(5-heptylpyrimidin-2-yl)-phenyl p-pentylbenzyl ether,
9% of p-(5-heptylpyrimidin-2-yl)-phenyl p-hexylbenzyl ether,
12% of p-(5-nonylpyrimidin-2-yl)-phenyl p-pentylbenzyl ether,
10% of p-(5-nonylpyrimidin-2-yl)-phenyl p-heptylbenzyl ether,
20% of 2-p-nonyloxyphenyl-5-nonylpyrimidine,
9% of 1-(trans-4-heptylcyclohexyl)-2-(p-(5-octyl-pyrimidin-2-yl)-phenyl)-ethane,
8% of 1-(trans-4-octylcyclohexyl)-2-(p-(5-nonylpyrimidin-2-yl)-phenylethane, 10% of optically active 1-(p-(2-octyloxycarbonyl)-phenyl)-2-(p-(5-heptylpyrimidin-2-yl)-phenyl)-ethane and 11% of 1-(p-heptyloxy-m-fluorophenyl)-2-(p-(5-heptyl-pyrimidin-2-yl)-phenyl)-ethane exhibits C 3° S$_c$* 72° Ch 93° I.

We claim:

1. A nitrogen-containing heterocyclic ester of the formula $$R^1—A^1—Z^1—A^2—R^2$$

wherein

R$^1$ and R$^2$ are each independently alkyl of 1 to 12 C-atoms, in which one or two non-adjacent CH$_2$ groups may be replaced by —O—, —CO—, —O—CO—, O—COO— and/or —CO—O—, and/or which may be monosubstituted by fluorine, chlorine or cyano, A$^1$ is —Pyr—Phe— or —Phe—Pyr— wherein —Phe— is 1,4-phenylene optionally substituted by one or two F atoms and —Pyr— is pyrimidine-2,5- or -5,2-diyl, A$^2$ and A$^3$ are each independently trans-1,4-cyclohexylene, or 1,4-phenylene which is unsubstituted or substituted by one or two of F, Cl, Br or CN, Z$^1$ is —CO—O— or —O—CO—, with the provisos that (1) said ester contains at least one laterally substituted 1,4-phenylene group and (2) when

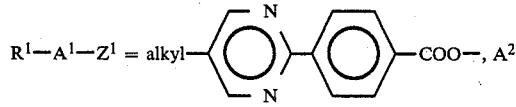

is 1,4-phenylene which is laterally substituted by fluorine or is 1,4-phenylene which is substituted in the position ortho to R$^2$ by Cl, Br or CN.

2. An ester of claim 1, wherein one of the radicals R$^1$ and R$^2$ is alkyl, —O-alkyl, oxaalkyl, —COO-alkyl, —OCO-alkyl or —CO-alkyl.

3. An ester of claim 1 wherein each of the groups R$^1$ and R$^2$ have 5, 6, 7, 8, 9, 10, 11 or 12 C atoms.

4. An ester of claim 3, wherein the alkyl radicals in the groups R$^1$ and R$^2$ are straight-chained.

5. An ester of claim 4, wherein at least one of the groups R$^1$ and R$^2$ is pentoxy, hexoxy, heptoxy, octoxy, nonoxy, decoxy, undecoxy, dodecoxy, 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl, 1,4-dioxaoctyl, 1,4-dioxanonyl or 1,4-dioxadecyl.

6. An optionally active ester of claim 1, wherein one of the groups R$^1$ and R$^2$ has the formula

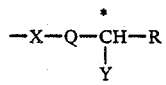

in which

X is —CO—O, O—CO—, —O—CO—O—, —CO—, —O— or a single bond,

Q is alkylene of 1 to 5 C-atoms or a single bond,

Y is CN, halogen, or methyl, and

R is alkyl of 1 to 18 C atoms, which is different from Y and in which one CH$_2$ group may be replaced by —O—, —CO—, —O—CO— or —O—CO—.

7. An ester of claim 6, wherein X is —O—, —CO—O— or O—CO—.

8. An ester of claim 6, wherein Q is —CH$_2$—CH$_2$—, —CH$_2$— or a single bond.

9. An ester of claim 6, wherein Y is CN, CH$_3$ or Cl.

10. An ester of claim 6, wherein R is straight-chain alkyl of 1 to 7 C atoms, in which the CH$_2$ group which is linked to the asymmetrical C atom may optionally be replaced by —O—, —O—CO— or —CO—O.

11. An ester of claim 6, wherein R$^2$ is the optically active radical.

12. An ester of claim 6, wherein R$^2$ is of the formula

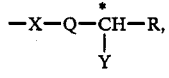

in which X is —O—, —CO—O— or —O—CO—, Q is —CH$_2$— or a single bond, Y is CH$_3$, and R is straight-chain alkyl of 1 to 7 C atoms in which the CH$_2$ group which is linked to the asymmetrical C atom is replaced by —O—, —CO—O— or —O—CO—.

13. An ester of claim 1, wherein R$^1$ and R$^2$ are each independently alkyl or alkoxy of 3 to 10 C atoms.

14. An ester of claim 1, wherein Z$^1$ is —O—CO—.

15. An ester of claim 1, wherein the laterally substituted phenylene group is a 1,4-phenylene group which is substituted by F.

16. An ester of claim 1, wherein —A$^1$— is of the formula

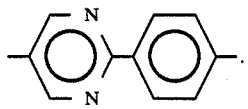

* * * * *